(12) United States Patent
Harding

(10) Patent No.: US 7,831,019 B2
(45) Date of Patent: Nov. 9, 2010

(54) SYSTEM AND METHODS FOR CHARACTERIZING A SUBSTANCE

(75) Inventor: Geoffrey Harding, Hamburg (DE)

(73) Assignee: Morpho Detection, Inc., Newark, CA (US)

( * ) Notice: Subject to any disclaimer, the term of this patent is extended or adjusted under 35 U.S.C. 154(b) by 62 days.

(21) Appl. No.: 12/006,010

(22) Filed: Dec. 28, 2007

(65) Prior Publication Data

US 2009/0168962 A1 Jul. 2, 2009

(51) Int. Cl.
*G01N 23/20* (2006.01)

(52) U.S. Cl. .............................. 378/70; 378/71; 378/86; 378/88

(58) Field of Classification Search ................... 378/70, 378/71, 86, 88
See application file for complete search history.

(56) References Cited

U.S. PATENT DOCUMENTS

| | | | |
|---|---|---|---|
| 4,963,746 A | 10/1990 | Morgan et al. | |
| 5,682,412 A | 10/1997 | Skillicorn et al. | |
| 6,807,248 B2 | 10/2004 | Milhara et al. | |
| 6,816,564 B2 | 11/2004 | Charles, Jr. et al. | |
| 6,917,396 B2 | 7/2005 | Hiraishi et al. | |
| 6,975,752 B2 | 12/2005 | Dixon et al. | |
| 7,283,613 B2 | 10/2007 | Harding | |
| 2006/0140340 A1* | 6/2006 | Kravis ........................ | 378/57 |
| 2007/0158573 A1 | 7/2007 | Deych | |
| 2007/0263770 A1 | 11/2007 | Harding | |
| 2007/0263771 A1 | 11/2007 | Harding | |

OTHER PUBLICATIONS

European Search Report, dated Mar. 11, 2009, from the European Patent Office for corresponding European patent application No. EP08172076 (8 pages).
XP002459483, Harding, Effective density and atomic number determined from diffraction profiles, Proceedings of the SPIE, SPIE, Bellingham, Virginia, USA, vol. 6319, Aug. 30, 2006, pp. 63190-1 through 63190-10 (10 pages).
XP002517126, Harding et al., Liquids identification with x-ray diffraction, Proceedings of the SPIE, SPIE, Bellingham, Virginia, USA, vol. 6707, Sep. 24, 2007, pp. 67070T-1 through 67070T-12 (12 pages).
Hubbell, J. H., Veigele, W. J., Briggs, E. A., Brown, R. T., Cromer, D. T., Howerton, R. J., Atomic Form Factors, Incoherent Scattering Functions and Photon Scattering Cross-sections, Journal of Physics and Chemical Reference Data, vol. 4, p. 471 (1975).
Erratum: Atomic Form Factors, Incoherent Scattering Functions, and Photon Scattering Cross Sections, Journal of Physics and Chemical Reference Data, vol. 6, p. 615 (1977).

* cited by examiner

*Primary Examiner*—Hoon Song
*Assistant Examiner*—Mona M Sanei
(74) *Attorney, Agent, or Firm*—Armstrong Teasdale LLP

(57) ABSTRACT

A system and methods for characterizing an unknown substance is described. One of the methods include determining an effective atomic number of the unknown substance as a first function of a first gradient of a first line.

19 Claims, 11 Drawing Sheets

SYSTEM AND METHODS FOR CHARACTERIZING A SUBSTANCE

FIELD OF THE INVENTION

The field of the invention relates generally to a system and methods for characterizing a substance and, more particularly, to a system and methods for determining an effective atomic number and a molecular interference function of the substance.

BACKGROUND OF THE INVENTION

The events of Sep. 11, 2001 instigated an urgency for more effective and stringent screening of airport baggage. The urgency for security expanded from an inspection of carry-on bags for knives and guns to a complete inspection of checked bags for a range of hazards with particular emphasis upon concealed explosives. X-ray imaging is a widespread technology currently employed for screening.

Identification systems based on X-ray diffraction (XRD) techniques provide an improved discrimination of the materials compared to that provided by the X-ray baggage scanners. The XRD identification systems measure d-spacings between lattice planes of micro-crystals in the materials. A "d-spacing" is a perpendicular distance between adjacent lattice planes in any of the materials.

However, the XRD identification systems for explosives detection and baggage scanning are not yet highly developed. Moreover, the diffraction techniques suffer from a false alarm problem for some classes of substances. There are certain types of explosives in which an explosive component cannot be identified by the XRD identification systems and the lack of identification leads to a high false alarm rate.

BRIEF DESCRIPTION OF THE INVENTION

A brief description of embodiments of a system and methods for characterizing a substance follows.

In one aspect, a method for characterizing an unknown substance is described. The method includes determining an effective atomic number of the unknown substance as a first function of a first gradient of a first line.

In another aspect, a method for characterizing a substance is described. The method includes determining an effective atomic number of the substance from a plurality of diffraction profiles.

In yet another aspect, a method for characterizing a substance is described. The method includes determining a relative molecular interference function of the substance from a plurality of diffraction profiles.

In another aspect, a system for characterizing an unknown substance is described. The system includes an X-ray source configured to generate X-rays, a detector configured to output a plurality of electrical signals by detecting the X-rays, and a processor configured to determine, based on the electrical signals, an effective atomic number of the unknown substance as a first function of a first gradient of a first line.

BRIEF DESCRIPTION OF THE DRAWINGS

FIG. 1 is an isometric view of an embodiment of a system for characterizing a substance.

FIG. 2 is block diagram of an embodiment of a system for characterizing a substance.

FIG. 3 is a block diagram of an embodiment of a system for characterizing a substance.

FIG. 4 is a block diagram of an embodiment of a system for generating an X-ray image.

FIG. 5 is an isometric view of an alternative embodiment of a system for characterizing a substance.

FIG. 6 is a flowchart of an embodiment of a method for characterizing a substance.

FIG. 7 is a continuation of the flowchart of FIG. 6.

FIG. 8 is a continuation of the flowchart of FIG. 7.

FIG. 9 is a continuation of the flowchart of FIG. 8.

FIG. 10 is a continuation of the flowchart of FIG. 7.

FIG. 11 is a continuation of the flowchart of FIG. 10.

FIG. 12 is a continuation of the flowchart of FIG. 11.

FIG. 13 shows an embodiment of a diffraction profile of a substance used within the system of FIG. 1 and an embodiment of a diffraction profile of a calibration substance.

FIG. 14 shows an embodiment of a logarithmic diffraction profile of gasoline.

FIG. 15 shows an embodiment of a logarithmic diffraction profile of sulphuric acid.

DETAILED DESCRIPTION OF THE INVENTION

While described in terms of detecting contraband including, without limitation, weapons, explosives, and/or narcotics, within baggage, the embodiments described herein can be used for any suitable diffraction imaging application.

Figure 1:
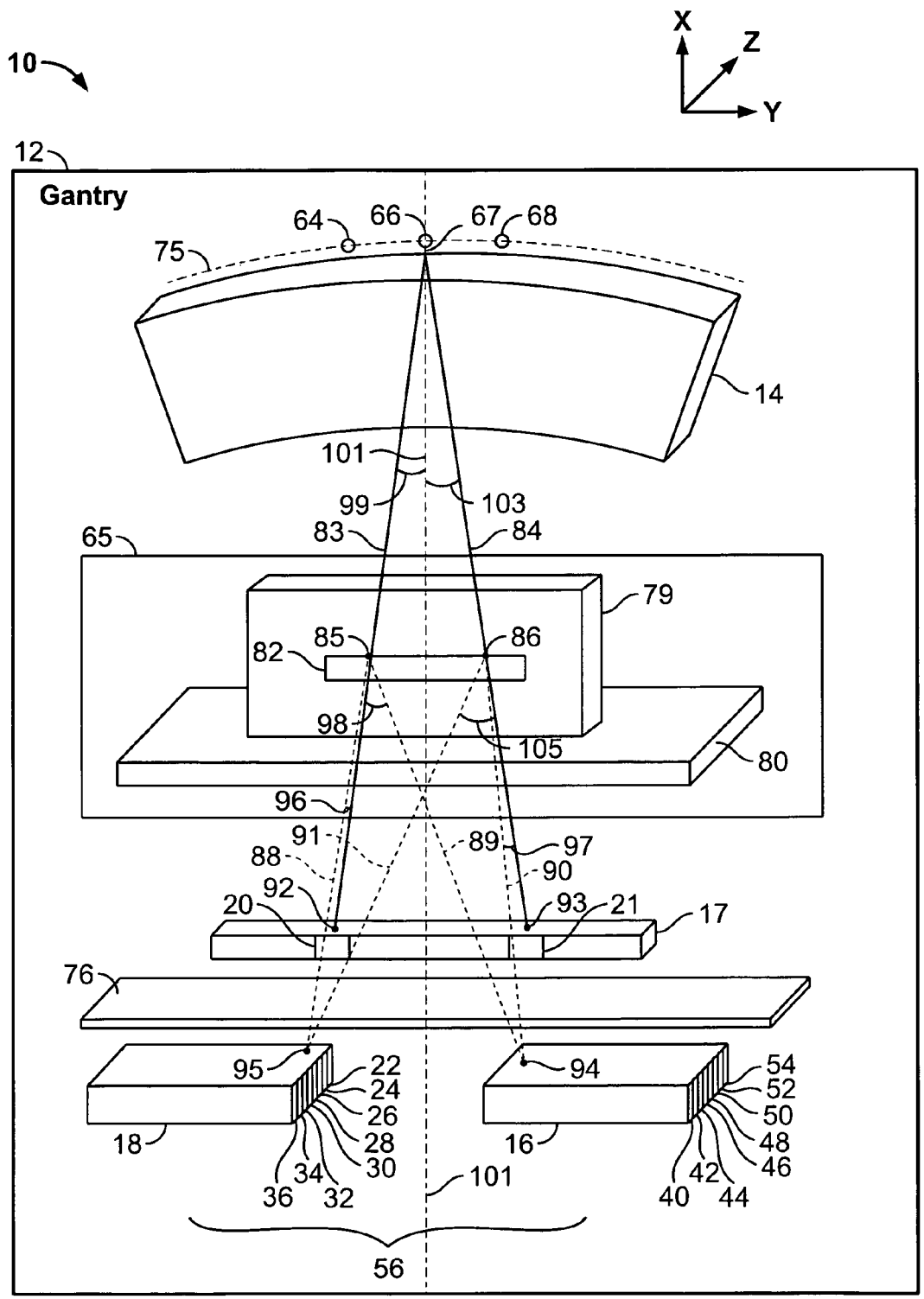
FIGS. 1-15 show embodiments of a system and methods for characterizing a substance.

FIG. 1 is an isometric view of an embodiment of a system 10 for characterizing a substance. System 10 includes a gantry 12. Gantry 12 includes a primary collimator 14, which is a multi-focus primary collimator, a scatter detector 16, a transmission detector 17, a scatter detector 18, and a secondary collimator 76. In an alternative embodiment, a single-focus primary collimator is used instead of primary collimator 14. Each scatter detector 16 and 18 is a segmented semiconductor detector.

Transmission detector 17 includes a plurality of detector elements, such as detector elements 20 and 21. Scatter detector 18 includes a plurality of detector cells or detector elements 22, 24, 26, 28, 30, 32, 34, and 36 for detecting coherent scatter. Scatter detector 16 includes a plurality of detector cells or detector elements 40, 42, 44, 46, 48, 50, 52, and 54 for detecting coherent scatter. Each scatter detector 16 and 18 includes any suitable number of detector elements, such as ranging from and including 5 to 1200 detector elements. For example, scatter detector 18 includes 5 detector elements in a z-direction parallel to a z-axis, and one detector element in a y-direction parallel to a y-axis. As another example, scatter detector 18 includes 20 detector elements in the z-direction, and 20 detector elements in the y-direction. As yet another example, scatter detector 18 includes 40 detector elements in the z-direction, and 30 detector elements in the y-direction. An x-axis, the y-axis, and the z-axis are located within an xyz co-ordinate system having an origin. The x-axis is perpendicular to the y-axis and the z-axis, the y-axis is perpendicular to the z-axis, and the x-axis is parallel to an x-direction. A number of detector elements within scatter detector 16 may be equal to a number of detector elements within scatter detector 18.

Scatter detector 16 is separate from scatter detector 18. For example, scatter detector 16 has a housing that is separate from a housing of scatter detector 18. As another example scatter detectors 16 and 18 are separated from each other by a gap. As yet another example, a shortest distance 56 between a center of scatter detector 16 and a center of scatter detector 18 ranges from and including 40 millimeters (mm) to 200 mm.

As another example, shortest distance 56 between a center of scatter detector 16 and a center of scatter detector 18 is 45 mm. As yet another example, shortest distance 56 between a center of scatter detector 16 and a center of scatter detector 18 is 125 mm. As still another example, shortest distance 56 between a center of scatter detector 16 and a center of scatter detector 18 is 195 mm. Scatter detector 16, scatter detector 18, and transmission detector 17 may be located in the same yz plane. The yz plane is formed by the y-axis and the z-axis. Each scatter detector 16 and scatter detector 18 may be separated from transmission detector 17 by a shortest distance ranging from and including 30 mm to 60 mm in the z-direction. As an example, each scatter detector 16 and scatter detector 18 is separated from transmission detector 17 by a shortest distance of 35 mm in the z-direction. As another example, each scatter detector 16 and scatter detector 18 is separated from transmission detector 17 by a shortest distance of 50 mm in the z-direction. As yet another example, each scatter detector 16 and scatter detector 18 is separated from transmission detector 17 by a shortest distance of 60 mm in the z-direction.

Gantry 12 further includes a plurality of X-ray sources 64, 66, and 68. In an alternative embodiment, gantry 12 includes any number, such as one, two, four, five, or ten X-ray sources. X-ray sources 64, 66, and 68, and transmission detector 17 form an inverse single-pass multi-focus imaging system. X-ray sources 64, 66, and 68 have an inverse fan-beam geometry that includes a symmetric location of the X-ray sources 64, 66, and 68 relative to the z-axis. X-ray sources 64, 66, and 68, are located parallel to and coincident with an arc 75. It is noted that in an alternative embodiment, system 10 includes a higher number, such as 10 or 20, or alternatively a lower number, such as 4 or 6, X-ray sources than that shown in FIG. 1. A center of transmission detector 17 is located at a center of a circle having arc 75. Each X-ray source 64, 66, and 68 is an X-ray source that includes a cathode and an anode. Alternatively, each X-ray source 64, 66, and 68 is an X-ray source that includes a cathode and all X-ray sources 64, 66, and 68 share a common anode.

A container 79 is placed on a support 80 between a set of X-ray sources 64, 66, and 68, and a set of scatter detectors 16 and 18. Container 79 and support 80 are located within an opening 65 of gantry 12. Examples of container 79 include a bag, a box, and an air cargo container. Examples of each X-ray source 64, 66, and 68 include a polychromatic X-ray source. Container 79 includes a substance 82. Examples of substance 82 include an organic explosive, an amorphous substance having a crystallinity of less than twenty five percent, a quasi-amorphous substance having a crystallinity at least equal to twenty-five percent and less than fifty percent, a partially crystalline substance having a crystallinity at least equal to fifty percent and less than one-hundred percent, and a crystalline substance having a crystallinity of one-hundred percent. Examples of the amorphous, quasi-amorphous, and partially crystalline substances include a gel explosive, a slurry explosive, an explosive including ammonium nitrate, and a special nuclear material. Examples of the special nuclear material include plutonium and uranium. Examples of support 80 include a table and a conveyor belt. An example of each scatter detector 16 and 18 includes a segmented detector fabricated from Germanium.

X-ray source 66 emits an X-ray beam 67 in an energy range, which is dependent on a voltage applied by a power source to X-ray source 66. Primary collimator 14 generates two primary beams 83 and 84, such as pencil beams, after collimating X-ray beam 67 from X-ray source 66. In an alternative embodiment, primary collimator 14 collimates X-ray beam 67 received from X-ray source 66 to generate a plurality, such as three or four, primary beams. A number of primary beams generated by primary collimator 14 is equal to, or alternatively, greater than a number of scatter detectors on one side of transmission detector 17 and on one side of the y-axis. Primary beams 83 and 84 pass through a plurality of points 85 and 86 on substance 82 within container 79 arranged on support 80 to generate scattered radiation 88, 89, 90, and 91. For example, primary beam 83 passes through point 85 to generate scattered radiation 88 and 89. As another example, primary beam 84 passes through point 86 to generate scattered radiation 90 and 91.

Secondary collimator 76 is located between support 80 and scatter detectors 16 and 18. Secondary collimator 76 includes a number of collimator elements, such as sheets, slits, or laminations, to ensure that scattered radiation arriving at scatter detectors 16 and 18 have constant scatter angles with respect to primary beams 83 and 84 and that a position of scatter detectors 16 and 18 permits a depth in container 79 at which the scattered radiation originated to be determined. For example, the collimator elements of secondary collimator 76 are arranged parallel to a direction of scattered radiation 88 and of scattered radiation 90 to absorb scattered radiation that is not parallel to the direction of scattered radiation 88 and of scattered radiation 90.

The number of collimator elements in secondary collimator 76 is equal to or alternatively greater than a number of detector elements of scatter detectors 16 and/or 18. The collimator elements are arranged such that scattered radiation between neighboring collimator elements is incident on one of the detector elements. The collimator elements of scatter detectors 16 and 18 are made of a radiation-absorbing material, such as steel, copper, silver, or tungsten.

Transmission detector 17 is positioned underneath support 80, and configured to measure an intensity of primary beam 83 at a point 92 on transmission detector 17 and an intensity of primary beam 84 at a point 93 on transmission detector 17. Moreover, scatter detectors 16 and 18 that measure photon energies of scattered radiation are positioned underneath support 80 and configured to measure photon energies of scattered radiation received by scatter detectors 16 and 18. Each scatter detector 16 and 18 measures the X-ray photons within scattered radiation received by scatter detectors 16 and 18 in an energy-sensitive manner by outputting a plurality of electrical output signals linearly dependent on a plurality of energies of the X-ray photons detected from within the scattered radiation. Scatter detector 16 measures scattered radiation 90 received at a point 94 on scatter detector 16 and scatter detector 18 measures scattered radiation 88 received at a point 95 on scatter detector 18. An example of a shortest distance between points 85 and 95 includes a distance ranging from and including 900 mm to 1100 mm. Another example of a shortest distance between points 85 and 95 includes a distance of 925 mm. Yet another example of a shortest distance between points 85 and 95 includes a distance of 1000 mm. Another example of a shortest distance between points 85 and 95 includes a distance of 1095 mm. An example of a distance between points 95 and 92 includes a distance ranging from and including 25 mm to 80 mm. Yet another example of a distance between points 95 and 92 includes a distance of 30 mm. Another example of a distance between points 95 and 92 includes a distance of 50 mm. Yet another example of a distance between points 95 and 92 includes a distance of 75 mm.

Scatter detectors 16 and 18 detect scattered radiation to generate a plurality of electrical output signals. Scatter detector 16 detects scattered radiation 90 generated upon intersection of primary beam 84 with point 86. Moreover, scatter detector 16 detects at least a portion of scattered radiation 89 generated upon intersection of primary beam 83 with point 85. Scatter detector 18 detects scattered radiation 88 generated upon intersection of primary beam 83 with point 85. Moreover, scatter detector 18 detects at least a portion of scattered radiation 91 generated upon intersection of primary beam 84 with point 86. A scatter angle 96 formed between primary beam 83 and scattered radiation 88 is equal to a scatter angle 97 formed between primary beam 84 and scattered radiation 90. An example of each scatter angle 96 and 97 includes an angle ranging from and including 0.025 radians to 0.045 radians. As another example, each scatter angle 96 and 97 includes an angle of 0.03 radians. As yet another example, each scatter angle 96 and 97 includes an angle of 0.04 radians. As still another example, each scatter angle 96 and 97 includes an angle of 0.045 radians. An example of a scatter angle 98 formed between primary beam 83 and scattered radiation 89 ranges from and including 0.05 radians to 0.09 radians. An example of scatter angle 98 includes 0.05 radians. Another example of scatter angle 98 includes 0.07 radians. Yet another example of scatter angle 98 includes 0.09 radians. Moreover, an example of a scatter angle 105 formed between primary beam 84 and scattered radiation 91 ranges from and including 0.05 radians to 0.09 radians. An example of scatter angle 105 includes 0.05 radians. Another example of scatter angle 105 includes 0.07 radians. Yet another example of scatter angle 105 includes 0.09 radians.

Scatter angle 98 is at least two times greater than scatter angles 96 and/or 97 and scatter angle 105 is at least two times greater than scatter angles 96 and/or 97. An angle 99 formed by primary beam 83 with respect to a center 101 between scatter detectors 16 and 18 is equal to an angle 103 formed by primary beam 84 with respect to center 101.

In an alternative embodiment, system 10 includes additional scatter detectors other than scatter detectors 16 and 18. The additional scatter detectors are placed on a side of transmission detector 17 that includes scatter detectors 16 and 18. Moreover, the additional scatter detectors are the same as scatter detectors 16 and 18. For example, any one of the additional scatter detectors has the same number of detector elements as that of scatter detectors 16 and/or 18. In yet another alternative embodiment, system 10 does not include scatter detector 16.

Figure 2:
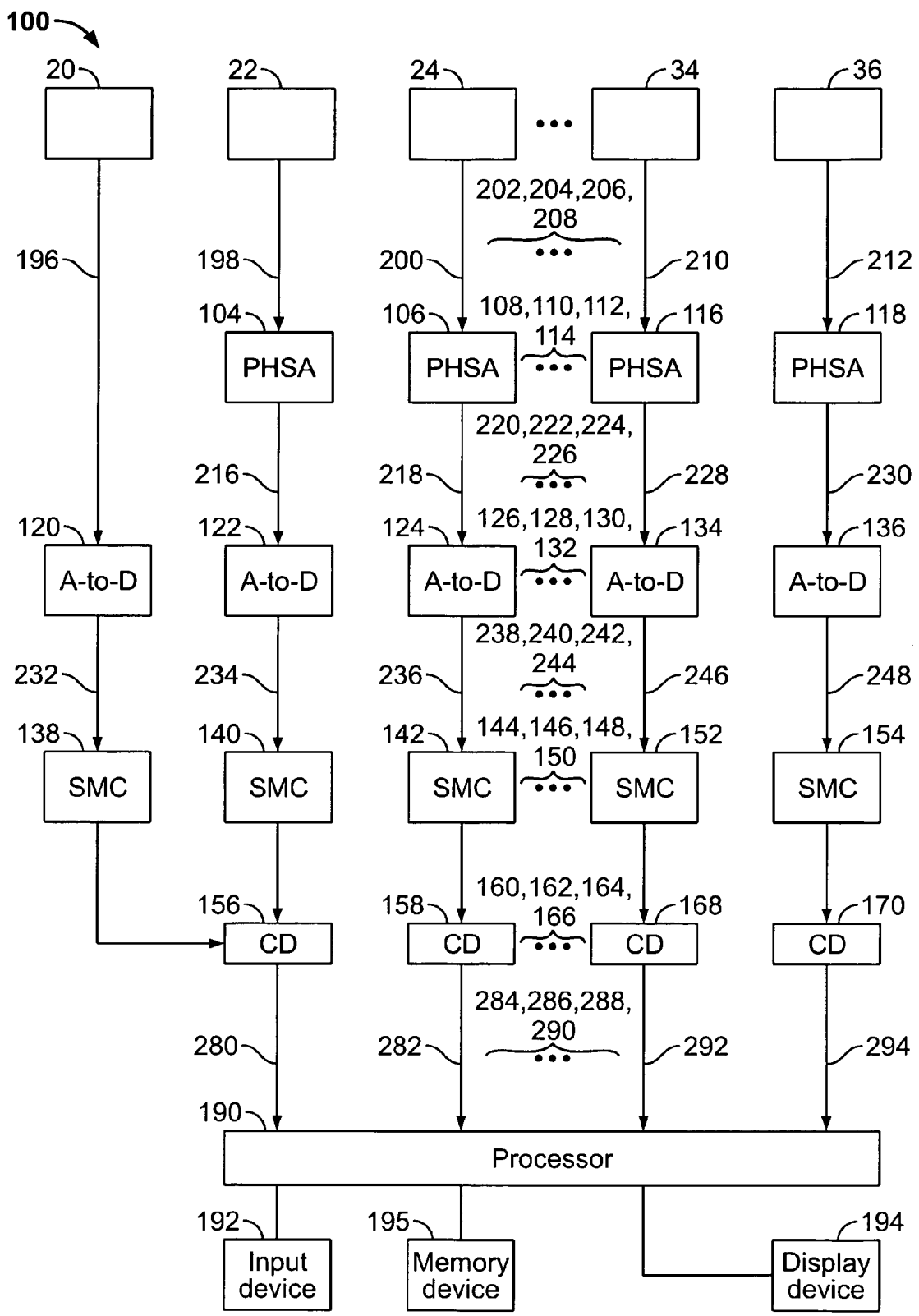

FIG. 2 is block diagram of an embodiment of a system 100 for characterizing a substance. System 100 includes detector element 20 of transmission detector 17, scatter detector elements 22, 24, 26, 28, 30, 32, 34, and 36, a plurality of pulse-height shaper amplifiers (PHSA) 104, 106, 108, 110, 112, 114, 116, and 118, a plurality of analog-to-digital (A-to-D) converters 120, 122, 124, 126, 128, 130, 132, 134, and 136, a plurality of spectrum memory circuits (SMCs) 138, 140, 142, 144, 146, 148, 150, 152, and 154 allowing pulse height spectra to be acquired, a plurality of correction devices (CDs) 156, 158, 160, 162, 164, 166, 168, and 170, a processor 190, an input device 192, a display device 194, and a memory device 195. As used herein, the term processor is not limited to just those integrated circuits referred to in the art as a processor, but broadly refers to a computer, a microcontroller, a microcomputer, a programmable logic controller, an application specific integrated circuit, and any other programmable circuit. The computer may include a device, such as, a floppy disk drive or CD-ROM drive, for reading data including the methods for characterizing a substance from a computer-readable medium, such as a floppy disk, a compact disc-read only memory (CD-ROM), a magneto-optical disk (MOD), and/or a digital versatile disc (DVD). In an alternative embodiment, processor 190 executes instructions stored in firmware. Examples of display device 194 include a liquid crystal display (LCD) and a cathode ray tube (CRT). Examples of input device 192 include a mouse and a keyboard. Examples of memory device 195 include a random access memory (RAM) and a read-only memory (ROM). An example of each correction device 156, 158, 160, 162, 164, 166, 168, and 170 include a divider circuit. Each spectrum memory circuit 138, 140, 142, 144, 146, 148, 150, 152, and 154 includes an adder and a memory device, such as a RAM or a ROM.

Detector element 20 is coupled to analog-to-digital converter 120, and detector elements 22, 24, 26, 28, 30, 32, 34, and 36 are coupled to pulse-height shaper amplifiers 104, 106, 108, 110, 112, 114, 116, and 118, respectively. Detector element 20 generates an electrical output signal 196 by detecting primary beam 83 and detector elements 22, 24, 26, 28, 30, 32, 34, and 36 generate a plurality of electrical output signals 198, 200, 202, 204, 206, 208, 210, and 212 by detecting scattered radiation. For example, detector element 22 generates electrical output signal 198 for each scattered X-ray photon incident on detector element 22. Each pulse-height shaper amplifier amplifies an electrical output signal received from a corresponding detector element. For example, pulse-height shaper amplifier 104 amplifies electrical output signal 198 and pulse-height shaper amplifier 106 amplifies electrical output signal 200. Pulse-height shaper amplifiers 104, 106, 108, 110, 112, 114, 116, and 118 have a gain factor determined by processor 190.

An amplitude of an electrical output signal output from a detector element is proportional to an energy of an X-ray quantum that is detected by the detector element to generate the electrical output signal. For example, an amplitude of electrical output signal 196 is proportional to an energy of an X-ray quantum in primary beam 83 detected by detector element 20. As another example, an amplitude of electrical output signal 198 is proportional to an energy of an X-ray quantum within scattered radiation that is detected by detector element 22.

A pulse-height shaper amplifier generates an amplified output signal by amplifying an electrical output signal generated from a detector element. For example, pulse-height shaper amplifier 104 generates an amplified output signal 216 by amplifying electrical output signal 198 and pulse-height shaper amplifier 106 generates an amplified output signal 218 by amplifying electrical output signal 200. Similarly, a plurality of amplified output signals 220, 222, 224, 226, 228, and 230 are generated. An analog-to-digital converter converts an output signal from an analog form to a digital form to generate a digital output signal. For example, analog-to-digital converter 120 converts electrical output signal 196 from an analog form to a digital format to generate a digital output signal 232, and analog-to-digital converter 122 converts amplified output signal 216 from an analog form to a digital format to generate a digital output signal 234. Similarly, a plurality of digital output signals 236, 238, 240, 242, 244, 246, and 248 are generated by analog-to-digital converters 124, 126, 128, 130, 132, 134, and 136, respectively. A digital value of a digital output signal generated by an analog-to-digital converter represents an amplitude of energy of a pulse of an amplified output signal. For example, a digital value of digital output signal 234 output by analog-to-digital converter 122 is a value of an amplitude of a pulse of amplified output signal 216. Each pulse is generated by an X-ray quantum, such as an X-ray photon.

An adder of a spectrum memory circuit adds a number of pulses in a digital output signal. For example, when analogto-digital converter 122 converts a pulse of amplified output signal 216 into digital output signal 234 to determine an amplitude of the pulse of amplified output signal 216, an adder within spectrum memory circuit 140 increments, by one, a value within a memory device of spectrum memory circuit 140. Accordingly, at an end of an X-ray examination of substance 82, a memory device within a spectrum memory circuit stores a number of X-ray quanta detected by a detector element. For example, a memory device within spectrum memory circuit 142 stores a number of X-ray photons detected by detector element 24 and each of the X-ray photons has an amplitude of energy or alternatively an amplitude of intensity that is determined by analog-to-digital converter 124.

A correction device receives a number of X-ray quanta that have a range of energies and are stored within a memory device of one of spectrum memory circuits 140, 142, 144, 146, 148, 150, 152, and 154, and divides the number of X-ray quanta by a number of X-ray quanta having the range of energies received from a memory device of spectrum memory circuit 138. For example, correction device 156 receives a number of X-ray photons having a range of energies from a memory device of spectrum memory circuit 140, and divides the number of X-ray photons by a number of X-ray photons having the range received from a memory device of spectrum memory circuit 138. Each correction device outputs a correction output signal that represents a range of energies within X-ray quanta received by a detector element. For example, correction device 156 outputs a correction output signal 280 representing an energy spectrum or alternatively an intensity spectrum within X-ray quanta detected by detector element 22. As another example, correction device 158 outputs correction output signal 282 representing an energy spectrum within X-ray quanta detector element 24. Similarly, a plurality of correction output signals 284, 286, 288, 290, 292, and 294 are generated by correction devices 160, 162, 164, 166, 168, and 170, respectively.

It is noted that a number of pulse-height shaper amplifiers 104, 106, 108, 110, 112, 114, 116, and 118 changes with a number of scatter detector elements 22, 24, 26, 28, 30, 32, 34, and 36. For example, five pulse-height shaper amplifiers are used for amplifying signals received from five corresponding scatter detector elements. As another example, four pulse-height shaper amplifiers are used for amplifying signals received from corresponding four scatter detector elements. Similarly, a number of analog-to-digital converters 120, 122, 124, 126, 128, 130, 132, 134, and 136 changes with a number of detector elements 20, 22, 24, 26, 28, 30, 32, 34, and 36 and a number of spectrum memory circuits 138, 140, 142, 144, 146, 148, 150, 152, and 154 changes with the number of detector elements 20, 22, 24, 26, 28, 30, 32, 34, and 36.

Figure 3:
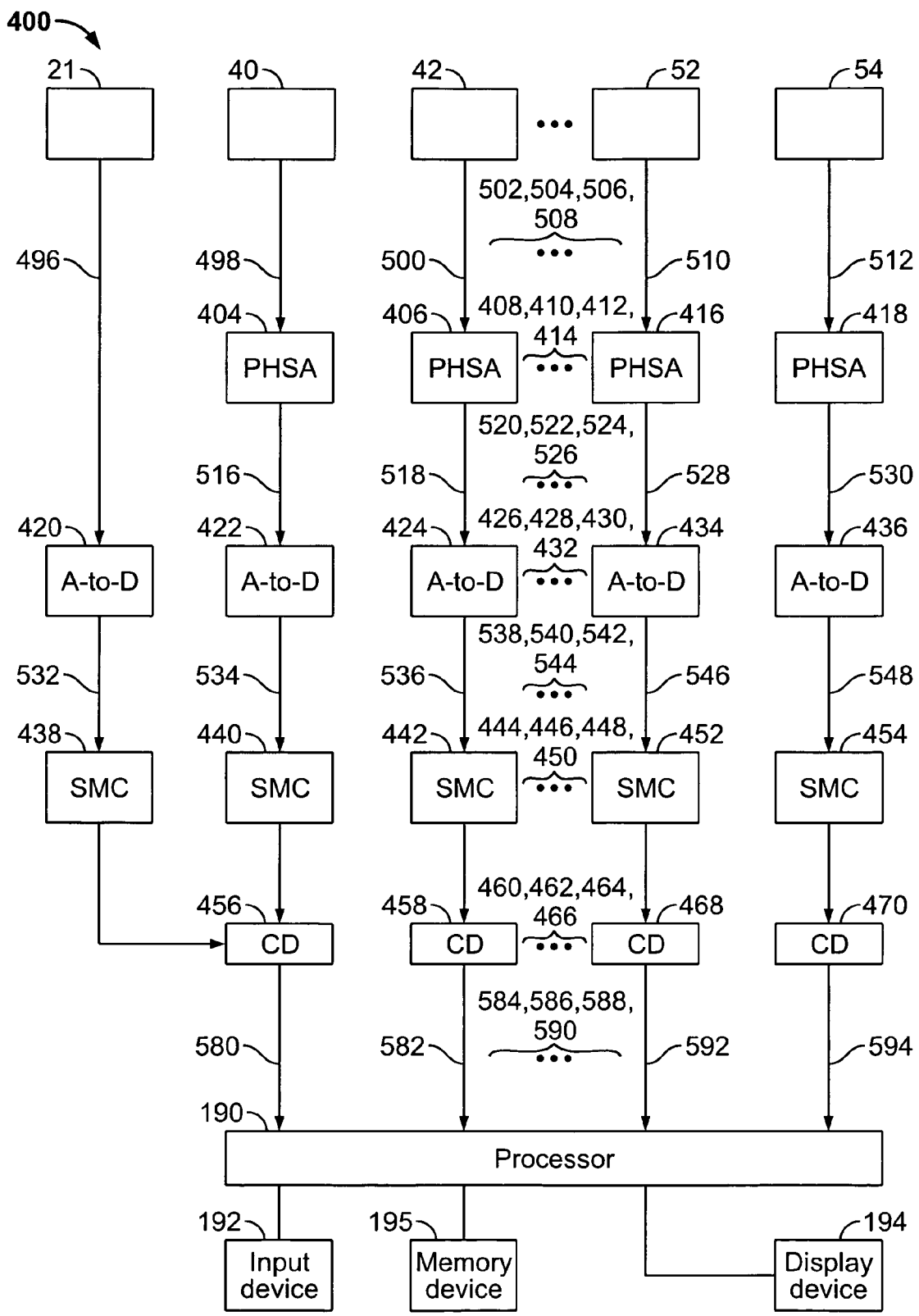

FIG. 3 is a block diagram of an embodiment of a system 400 for characterizing a substance. System 400 includes detector element 21 of transmission detector 17, scatter detector elements 40, 42, 44, 46, 48, 50, 52, and 54, a plurality of pulse-height shaper amplifiers (PHSA) 404, 406, 408, 410, 412, 414, 416, and 418, a plurality of analog-to-digital (A-to-D) converters 420, 422, 424, 426, 428, 430, 432, 434, and 436, a plurality of spectrum memory circuits (SMCs) 438, 440, 442, 444, 446, 448, 450, 452, and 454 allowing pulse height spectra to be acquired, a plurality of correction devices (CDs) 456, 458, 460, 462, 464, 466, 468, and 470, processor 190, input device 192, display device 194, and memory device 195. An example of each correction device 456, 458, 460, 462, 464, 466, 468, and 470 include a divider circuit.

Each spectrum memory circuit 438, 440, 442, 444, 446, 448, 450, 452, and 454 includes an adder and a memory device, such as a RAM or a ROM.

Transmission detector element 21 generates an electrical output signal 496 by detecting primary beam 84 and scatter detector elements 40, 42, 44, 46, 48, 50, 52, and 54 generate a plurality of electrical output signals 498, 500, 502, 504, 506, 508, 510, and 512 by detecting scattered radiation. For example, transmission detector element 21 generates electrical output signal 496 for X-ray photons incident on transmission detector element 21. Scatter detector elements 40, 42, 44, 46, 48, 50, 52, and 54 are coupled to pulse-height shaper amplifiers 404, 406, 408, 410, 412, 414, 416, and 418, respectively. Each pulse-height shaped amplifier amplifies an electrical output signal received from a corresponding detector element. For example, pulse-height shaper amplifier 404 amplifies electrical output signal 498. Pulse-height shaper amplifiers 404, 406, 408, 410, 412, 414, 416, and 418 have a gain factor determined by processor 190.

An amplitude of an electrical output signal output from a detector element is proportional to an energy of an X-ray quantum that is detected by the detector element to generate the electrical output signal. For example, an amplitude of electrical output signal 496 is proportional to an energy of an X-ray quantum in primary beam 84 detected by detector element 21. As another example, an amplitude of electrical output signal 498 is proportional to an energy of an X-ray quantum within scattered radiation that is detected by detector element 40.

A pulse-height shaper amplifier generates an amplified output signal by amplifying an electrical output signal generated from a detector element. For example, pulse-height shaper amplifier 404 generates an amplified output signal 516 by amplifying electrical output signal 498 and pulse-height shaper amplifier 406 generates an amplified output signal 518 by amplifying electrical output signal 500. Similarly, a plurality of amplified output signals 520, 522, 524, 526, 528, and 530 are generated. An analog-to-digital converter converts an output signal from an analog form to a digital form to generate a digital output signal. For example, analog-to-digital converter 420 converts electrical output signal 496 from an analog form to a digital format to generate a digital output signal 532 and analog-to-digital converter 422 converts amplified output signal 516 from an analog form to a digital format to generate a digital output signal 534. Similarly, a plurality of digital output signals 536, 538, 540, 542, 544, 546, and 548 are generated by analog-to-digital converters 424, 426, 428, 430, 432, 434, and 436, respectively. A digital value of a digital output signal generated by an analog-to-digital converter represents an amplitude of energy or alternatively an amplitude of intensity of a pulse of an amplified output signal. For example, a digital value of digital output signal 534 output by analog-to-digital converter 422 is a value of an amplitude of a pulse of amplified output signal 516.

An adder of a spectrum memory circuit adds a number of pulses in a digital output signal. For example, when analog-to-digital converter 422 converts a pulse of amplified output signal 516 into digital output signal 534 to determine an amplitude of the pulse of amplified output signal 516, an adder within spectrum memory circuit 440 increments, by one, a value within a memory device of spectrum memory circuit 440. Accordingly, at an end of an X-ray examination of substance 82, a memory device within a spectrum memory circuit stores a number of X-ray quanta detected by a detector element. For example, a memory device within spectrum memory circuit 442 stores a number of X-ray photons detected by detector element 42 and each of the X-ray photons has an amplitude of energy that is determined by analog-to-digital converter 424.

A correction device receives a number of X-ray quanta that have a range of energies and are stored within a memory device of one of spectrum memory circuits 440, 442, 444, 446, 448, 450, 452, and 454, and divides the number of X-ray quanta by a number of X-ray quanta having the range of energies received from a memory device of spectrum memory circuit 438. For example, correction device 456 receives a number of X-ray photons having a range of energies from a memory device of spectrum memory circuit 440, and divides the number of X-ray photons by a number of X-ray photons having the range received from a memory device of spectrum memory circuit 438. Each correction device outputs a correction output signal that represents a range of energies within X-ray quanta received by a corresponding detector element. For example, correction device 456 outputs a correction output signal 580 representing an energy spectrum, or alternatively an intensity spectrum within X-ray quanta detected by detector element 40. As another example, correction device 458 outputs correction output signal 582 representing an energy spectrum within X-ray quanta detected by detector element 42. Similarly, a plurality of correction output signals 584, 586, 588, 590, 592, and 594 are generated by correction devices 460, 462, 464, 466, 468, and 470, respectively.

Processor 190 receives correction output signals 280, 282, 284, 286, 288, 290, 292, 294, 580, 582, 584, 586, 588, 590, 592, and 594 to generate a momentum transfer x, measured in inverse nanometers ($nm^{-1}$), from an energy spectrum r(E) of energy E of X-ray quanta within scattered radiation detected by scatter detectors 16 and 18 (shown in FIG. 1). Processor 190 generates the momentum transfer x by applying $$x = (E/hc)\sin(\theta/2) \quad \text{Eq. (1)}$$

where c is a speed of light, h is Planck's constant, and $\theta$ represents a constant scatter angle of X-ray quanta of scattered radiation detected by scatter detectors 16 and 18. Examples of $\theta$ include scatter angles 96 and 97 (shown in FIG. 1). Processor 190 relates the energy E to the momentum transfer x by equation (1). Mechanical dimensions of secondary collimator 76 (shown in FIG. 1) defines the scatter angle $\theta$. The secondary collimator 76 restricts scattered radiation that does not have the scatter angle $\theta$. Processor 190 receives the scatter angle $\theta$ from a user, such as a human being, via input device 192. Processor 190 generates a diffraction profile of substance 82 (shown in FIG. 1) by calculating a number of scatter X-ray photons that are detected by scatter detectors 16 and 18 and by plotting the number of scatter X-ray photons versus the momentum transfer x.

It is noted that a number of pulse-height shape amplifiers 404, 406, 408, 410, 412, 414, 416, and 418 changes with a number of scatter detector elements 40, 42, 44, 46, 48, 50, 52, and 54. For example, five pulse-height shaper amplifiers are used for amplifying signals received from five corresponding scatter detector elements. As another example, four pulse-height shaper amplifiers are used for amplifying signals received from four corresponding scatter detector elements. Similarly, a number of analog-to-digital converters 420, 422, 424, 426, 428, 430, 432, 434, and 436 changes with a number of detector elements 21, 40, 42, 44, 46, 48, 50, 52, and 54, and a number of spectrum memory circuits 438, 440, 442, 444, 446, 448, 450, 452, and 454 changes with the number of detector elements 21, 40, 42, 44, 46, 48, 50, 52, and 54.

Figure 4:
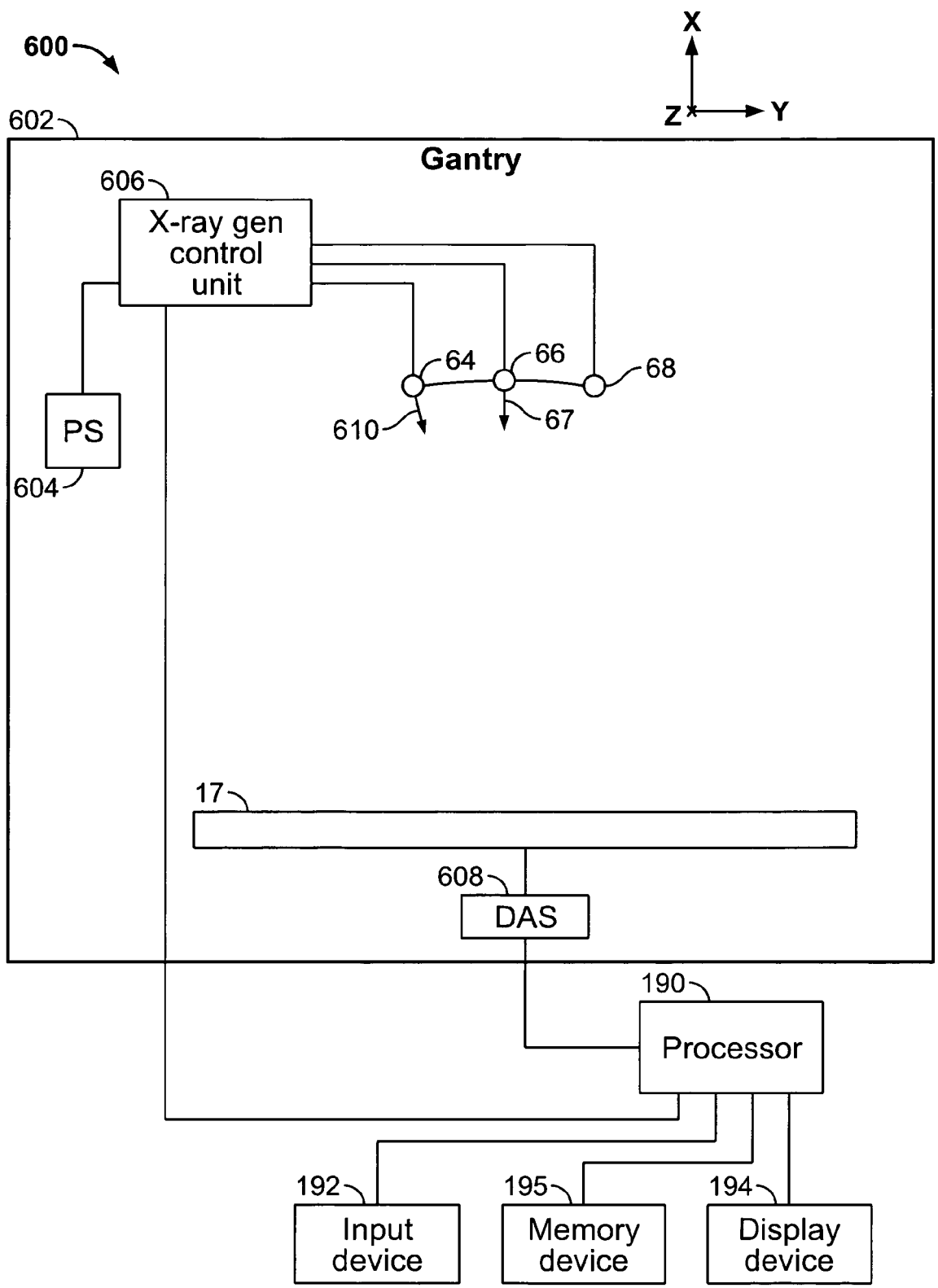

FIG. 4 is a block diagram of an embodiment of a system 600 for characterizing a substance. System 600 includes a gantry 602, processor 190, input device 192, display device 194, and memory device 195. Gantry 602 is an example of gantry 12 (shown in FIG. 1). Gantry 602 includes a power supply 604, an X-ray generation control unit 606, X-ray sources 64, 66, and 68, a data acquisition system (DAS) 608, and transmission detector 17. Alternatively, power supply 604 is located outside gantry 602.

X-ray generation control unit 606 includes a pulse generator (not shown) that is coupled to processor 190 and that receives power from power supply 604. Power supply 604 is coupled to X-ray sources 64, 66, and 68 to supply power to X-ray sources 64, 66, and 68.

Processor 190 issues a command, such as a first on command, a second on command, a first off command, and/or a second off command. Upon receiving the first on command from processor 190, the pulse generator generates a pulse and transmits the pulse to X-ray source 66. Upon receiving a pulse from the pulse generator, X-ray source 66 generates X-ray beam 67 under a potential applied by power supply 604. Similarly, upon receiving the first off command signal from processor 190, the pulse generator stops transmitting a pulse to X-ray source 66 and X-ray source 66 stops generating X-ray beam 67. Furthermore, upon receiving the second on command signal from processor 190, the pulse generator generates and transmits a pulse to any one of the remaining X-ray sources 64 and 68, and any one of the remaining X-ray sources 64 and 68 generates an X-ray beam. For example, upon receiving the second on command signal from processor 190, the pulse generator generates and transmits a pulse to X-ray source 64 and X-ray source 64 generates an X-ray beam 610. In this example, upon receiving the second off command signal from processor 190, the pulse generator stops transmitting a pulse to X-ray source 64, and X-ray source 64 stops generating an X-ray beam.

DAS 608 samples analog data, such as electrical output signals, generated from a plurality of detector elements, including detector elements 20 and 21, of transmission detector 17 and converts the analog data to a plurality of digital signals for subsequent processing.

Figure 5:
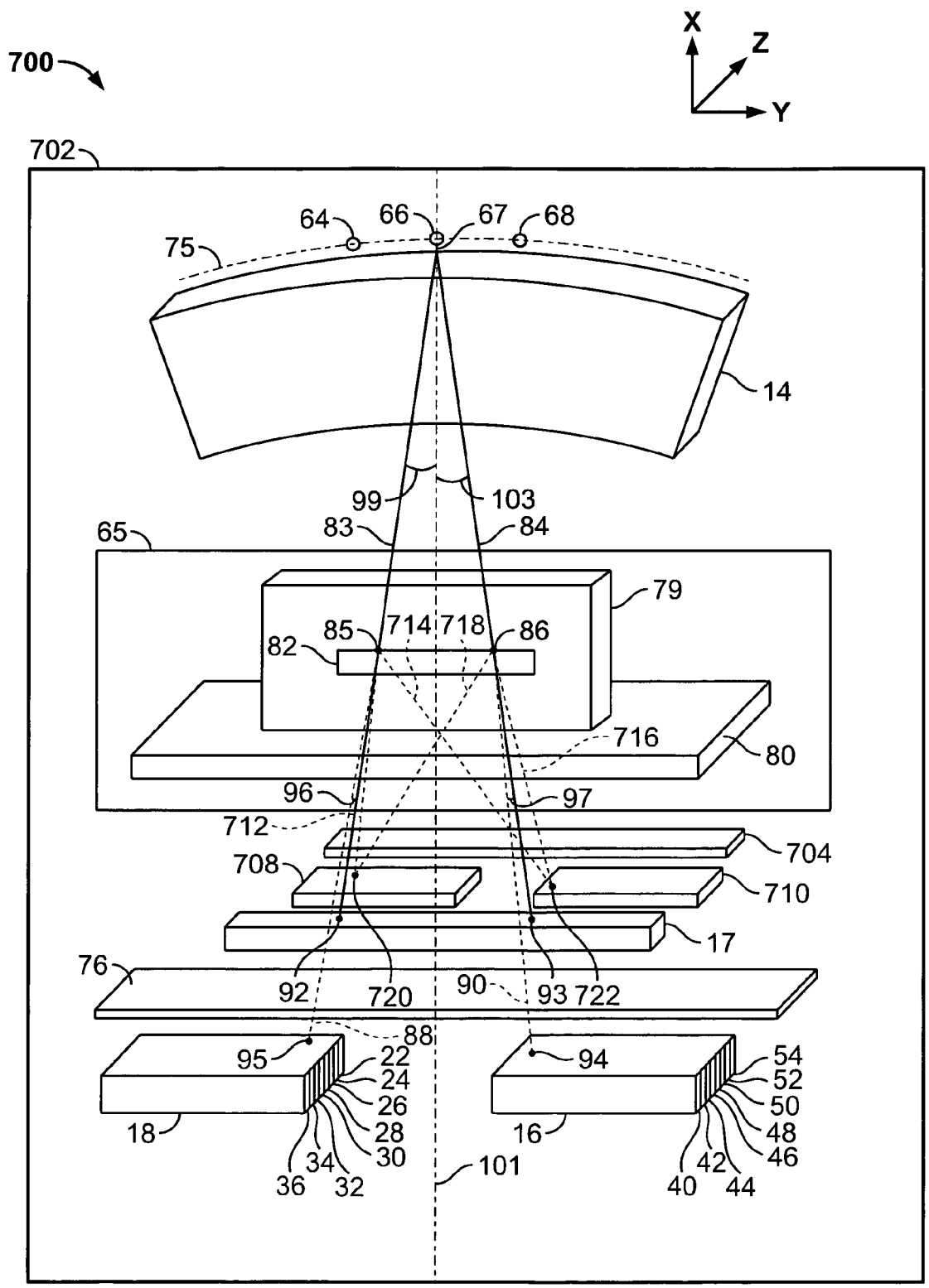
Figure 6:
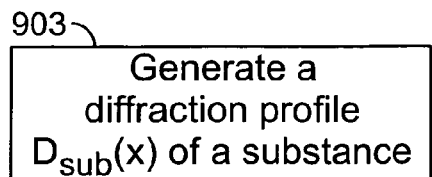
Figure 6:
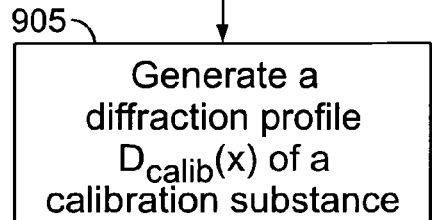
Figure 8:
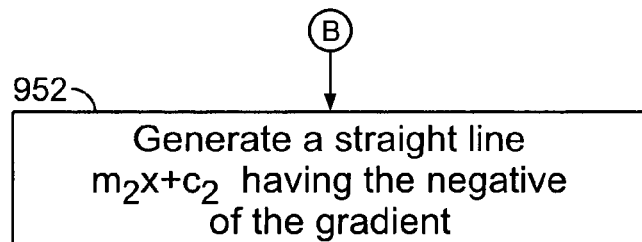
Figure 8:
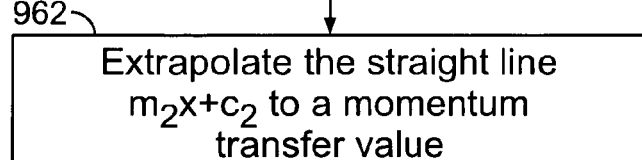
Figure 8:
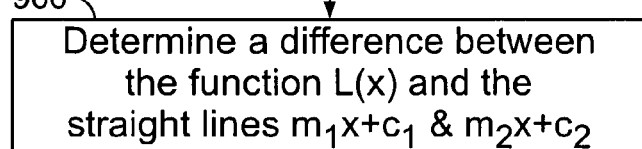
Figure 8:
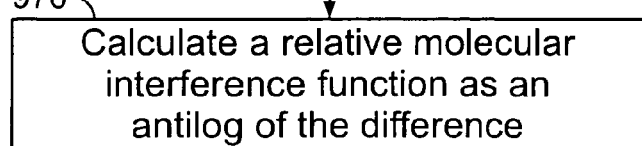

FIG. 5 is an isometric view of another embodiment of a system 700 for identifying a substance. System 700 includes a gantry 702. Gantry 702 includes X-ray sources 64, 66, and 68, primary collimator 14, secondary collimator 76, scatter detectors 16 and 18, transmission detector 17, a secondary collimator 704, and a plurality of scatter detectors 708 and 710 that detect coherent scatter. Gantry 702 is an example of gantry 12 (shown in FIG. 1). In one embodiment, secondary collimator 704 has the same structure as that of secondary collimator 76. Scatter detectors 708 and 710 are located on a side of transmission detector 17 and opposite to a side where scatter detectors 16 and 18 are located. A number of scatter detectors on a side of transmission detector 17 may be the same as a number of scatter detectors on another side of transmission detector 17. For example, if five scatter detectors are placed on a first side of transmission detector 17 where scatter detectors 16 and 18 are placed, five scatter detectors may be placed on the opposite second side of transmission detector 17 where scatter detectors 708 and 710 are placed. A shortest distance between a center of scatter detector 708 and a center of scatter detector 710 may be the same as shortest distance 56 between a center of scatter detector 16 and a center of scatter detector 18. Scatter detectors 708 and 710 are separated from each other by a gap. In one embodiment, each scatter detector 708 and 710 may have the same number of detector elements as scatter detector 16.

Primary beams 83 and 84 pass through points 85 and 86 on substance 82 to generate to generate scattered radiation 88 (FIG. 1), 89 (FIG. 1), 90 (FIG. 1), 91 (FIG. 1), 712, 714, 716, and 718. For example, primary beam 83 passes through point 85 on substance 82 to generate scattered radiation 88 (FIG. 1), 89 (FIG. 1), 712, and 714. As another example, primary beam 84 passes through point 86 on substance 82 to generate scattered radiation 90 (FIG. 1), 91 (FIG. 1), 716, and 718.

Secondary collimator 704 is located between support 80 and scatter detectors 708 and 710. Secondary collimator 704 includes a number of collimator elements to ensure that scattered radiation arriving at scatter detectors 708 and 710 have constant scatter angles with respect to primary beams 83 and 84. For example, the collimator elements of secondary collimator 704 are arranged parallel to a direction of scattered radiation 712 and of scattered radiation 716 to absorb scattered radiation that is not parallel to the direction of scattered radiation 712 and of scattered radiation 716.

The number of collimator elements in secondary collimator 704 is equal to or, alternatively, greater than a number of detector elements of scatter detectors 708 or 710. The collimator elements are arranged such that scattered radiation between neighboring collimator elements is incident on one of the detector elements. The collimator elements of scatter detectors 708 and 710 are made of a radiation-absorbing material, such as a copper alloy or a silver alloy.

Underneath support 80, scatter detectors 708 and 710 are positioned and configured to measure photon energies of scattered radiation detected by scatter detectors 708 and 710. Scatter detectors 16 and 18, transmission detector 17, and scatter detectors 708 and 710 may lie in the same yz plane. Each scatter detector 708 and 710 measures the X-ray photons within scattered radiation in an energy-sensitive manner by outputting a plurality of electrical output signals linearly dependent on a plurality of energies of the X-ray photons detected from within scattered radiation. Scatter detector 708 measures scattered radiation 712 received at a point 720 on scatter detector 708 and scatter detector 710 measures scattered radiation 716 received at a point 722 on scatter detector 710.

Scatter detectors 708 and 710 detect scattered radiation to generate a plurality of electrical output signals. Scatter detector 708 detects scattered radiation 712 generated upon intersection of primary beam 83 with point 85. Moreover, scatter detector 708 detects scattered radiation 718 generated upon intersection of primary beam 84 with point 86. Scatter detector 710 detects scattered radiation 716 generated upon intersection of primary beam 84 with point 86. Moreover, scatter detector 710 detects at least a portion of scattered radiation 714 generated upon intersection of primary beam 83 with point 85. A scatter angle formed between primary beam 83 and scattered radiation 712 is equal to a scatter angle formed between primary beam 84 and scattered radiation 716. In an alternative embodiment, system 700 does not include secondary collimators 76 and/or 704.

Scatter detector 708 is connected to a system similar to system 100 (shown in FIG. 2) to generate a plurality of correction output signals, such as correction output signals 280, 282, 284, 286, 288, 290, 292, and 294 (shown in FIG. 2). Moreover, scatter detector 710 is connected to a system similar to system 400 (FIG. 3) to generate a plurality of correction output signals, such as correction output signals 580, 582, 584, 586, 588, 590, 592, and 594 (shown in FIG. 3). Processor 190 receives the correction output signals generated by the system that is similar to system 100 and that is connected to scatter detector 708, and the correction output signals generated by the system that is similar to system 400 and that is connected to scatter detector 710, and generates a diffraction profile of substance 82.

Figure 13:
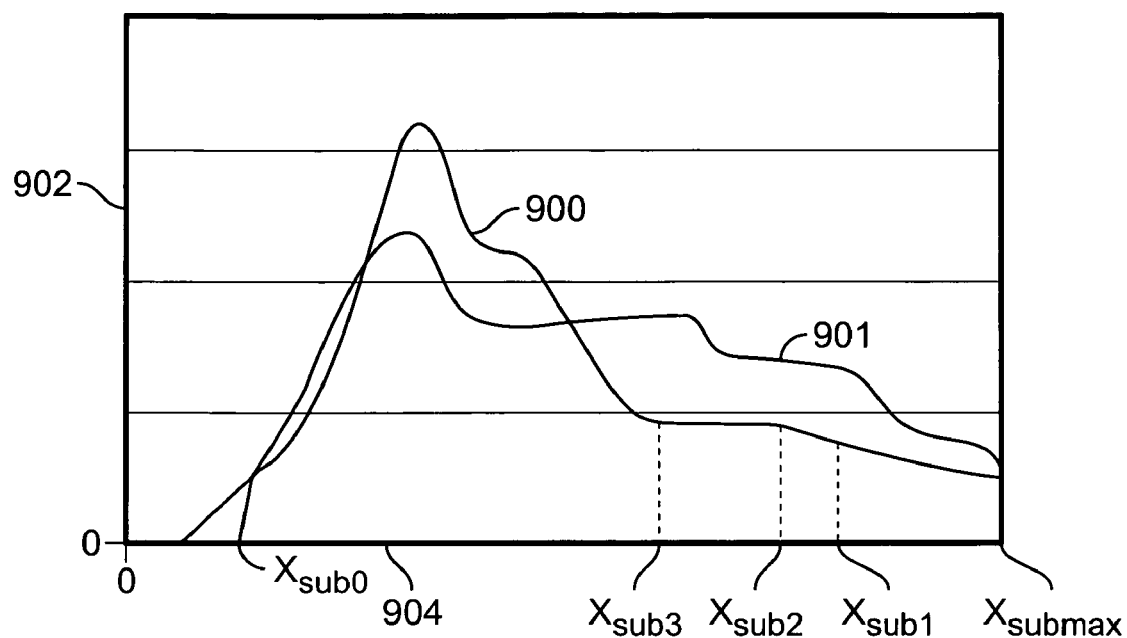

FIGS. 6-12 are a flowchart of an embodiment of a method for characterizing a substance and FIG. 13 shows a plurality of graphs 900 and 901. Graph 900 is a diffraction profile $D_{sub}(x)$ of substance 82 that is generated 903 by processor 190. Graph 900 is a histogram having a plurality of intensity values at a plurality of momentum transfer values, such as $x_{sub1}$, $x_{sub2}$, and $x_{sub3}$, of the momentum transfer x. As an example, when an operating voltage of X-ray source 67 is 160 kilovolts (kV), processor 190 calculates, by applying equation (1), an energy value $E_1$ of the energy E to be 160 keV, calculates, by applying equation (1), an energy value $E_2$ of the energy E to be 140 keV, and calculates, by applying equation (1), an energy value $E_3$ of the energy value E to be photon energy 120 keV. In this example, the photon energy values $E_1$, $E_2$, and $E_3$ correspond, through equation (1), to $x_{sub1}$ of four inverse nanometers, to $x_{sub2}$ of 3.5 inverse nanometers, and to $x_{sub3}$ of three inverse nanometers, respectively. Graph 900 represents a histogram of a number of X-ray photons detected by scatter detectors 16 and 18 versus the momentum transfer x of the X-ray photons.

Graph 901 is a diffraction profile $D_{calib}(x)$ of a calibration substance, such as white scatterer. An example of the white scatterer includes a combination of Lucite chippings, Cellulose paste, and water. The diffraction profile of the calibration substance is generated 905 in a similar manner as generation 903 of $D_{sub}(x)$. For example, the white scatterer is placed periodically, such as once each month or every 15 days, on a table within an object space, such as opening 65, of system 700, and is moved within the object space. In the example, upon receiving the correction output signals generated by the system that is similar to system 100 (shown in FIG. 2) and that is connected to scatter detector 708, and receiving the correction output signals generated by the system that is similar to system 400 (shown in FIG. 3) and that is connected to scatter detector 710, processor 190 generates the diffraction profile $D_{calib}(x)$ representing a number of photons detected by scatter detectors 708 and 710 versus the momentum transfer x. Graph 901 is a histogram having a plurality of intensity values at a plurality of momentum transfer values of the momentum transfer x when the calibration substance is placed within system 10. Graph 901 represents a histogram of a number of X-ray photons detected by scatter detectors 708 and 710 versus the momentum transfer x of the X-ray photons when the calibration substance is placed within system 10.

A number of X-ray photons detected by scatter detectors 16 and 18 or scatter detectors 708 and 710 is plotted along an ordinate 902 and a momentum transfer x is plotted along an abscissa 904. As an example, abscissa 904 extends from and includes zero inverse nanometers ($nm^{-1}$) to 10 $nm^{-1}$. An example of a total number of bins of numbers of X-ray photons plotted on ordinate 902 lies between 64 and 1024. An example of a number of X-ray photons detected by each scatter detector 16, 18, 708, and 710 per examination lies between 1000 and 100,000.

The diffraction profile $D_{sub}(x)$ ranging from $x \geq 3$ $nm^{-1}$ is generally dominated by coherent scatter from free atoms of substance 82. In a tip region, extending from $x_{sub1}$ to $x_{sub3}$, of graph 900, an intensity of scattered radiation is proportional to a product of density, such as a mean density, of substance 82 and a power, such as ranging between 2.5 and 3.5, of a mean atomic number of a plurality of materials within substance 82.

Figure 7:
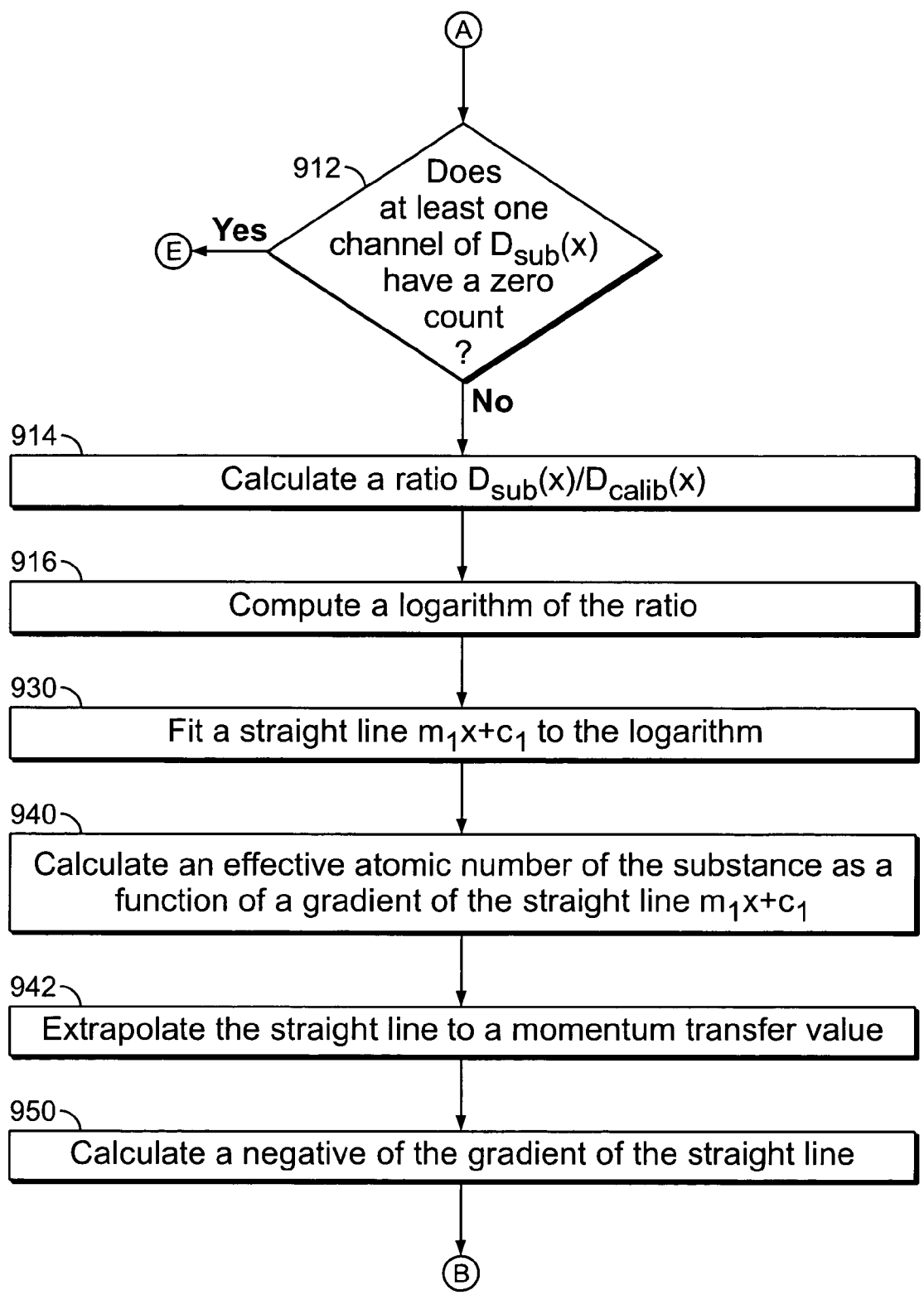
Figure 9:
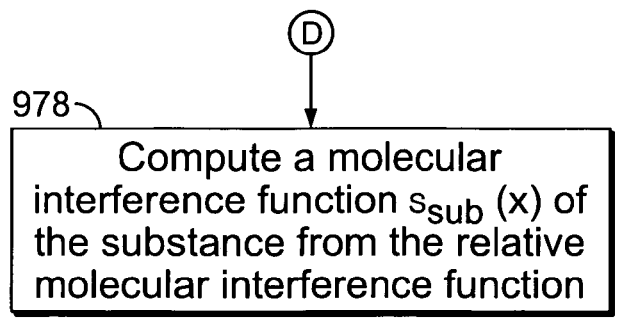

Referring to FIG. 7, processor 190 determines 912 whether at least one channel of the diffraction profile $D_{sub}(x)$ has a zero count of photons. In order to make such determination, processor 190 determines 912 to start with a channel that is assigned a momentum transfer value $x_{submax}$, as shown in FIG. 13. A channel is assigned a set of momentum transfer values on abscissa 904. An example of the set of momentum transfer values within a channel includes a range from and including 0.25 $nm^{-1}$ to 0.5 $nm^{-1}$. Another example of the set of momentum transfer values within a channel includes a range from and including 0.5 $nm^{-1}$ to 1 $nm^{-1}$. Yet another example of a set of momentum transfer values within a channel includes a momentum transfer value of 1.5 $nm^{-1}$. An example of a channel of the diffraction profile $D_{sub}(x)$, having a zero count of photons, includes a channel with a momentum transfer value $x_{sub0}$, as shown in FIG. 13. Another example of a channel of the diffraction profile $D_{sub}(x)$, having a non-zero count of photons includes a channel with the momentum transfer value of $x_{submax}$, as shown in FIG. 13.

Upon determining 912 that none of the channels of the diffraction profile $D_{sub}(x)$ have a zero count, processor 190 calculates 914 a ratio $D_{sub}(x)/D_{calib}(x)$ of the diffraction profiles 900 and 901. The ratio $D_{sub}(x)/D_{calib}(x)$ is a normalized profile function. Processor 190 further computes 916 a logarithm of the ratio $D_{sub}(x)/D_{calib}(x)$ as a function $$L_{sub}(x)=\log_e [D_{sub}(x)/D_{calib}(x)] \quad \text{Eq. (2)}$$

where the function $L_{sub}(x)$ is a logarithmic profile ratio.

Figure 14:
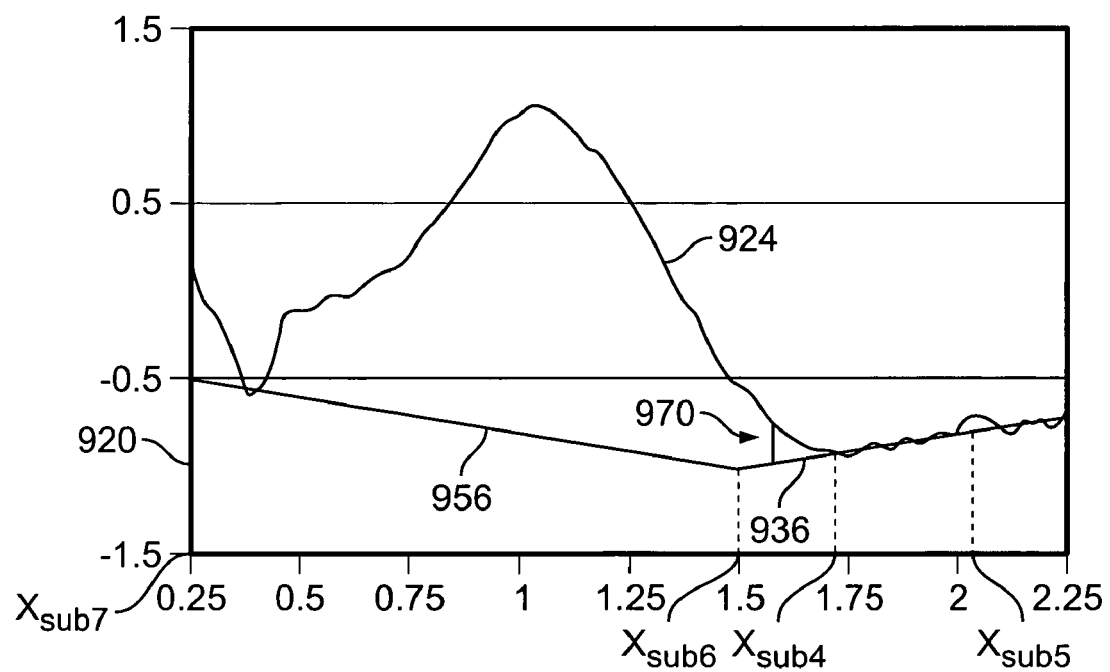

FIG. 14 shows a graph 924, which is a function $L_{gas}(x)$ and an example of the function $L_{sub}(x)$. Processor 190 generates graph 924 as a logarithm, to the base e, of a ratio of a diffraction profile $D_{gas}(x)$ of gasoline and the diffraction profile $D_N(x)$ versus the momentum transfer x. Gasoline, referred to herein as gas, is an example of substance 82. Processor 190 plots $\log_e [D_{gas}(x)/D_N(x)]$ on ordinate 920 and plots the momentum transfer x on abscissa 904.

Figure 15:
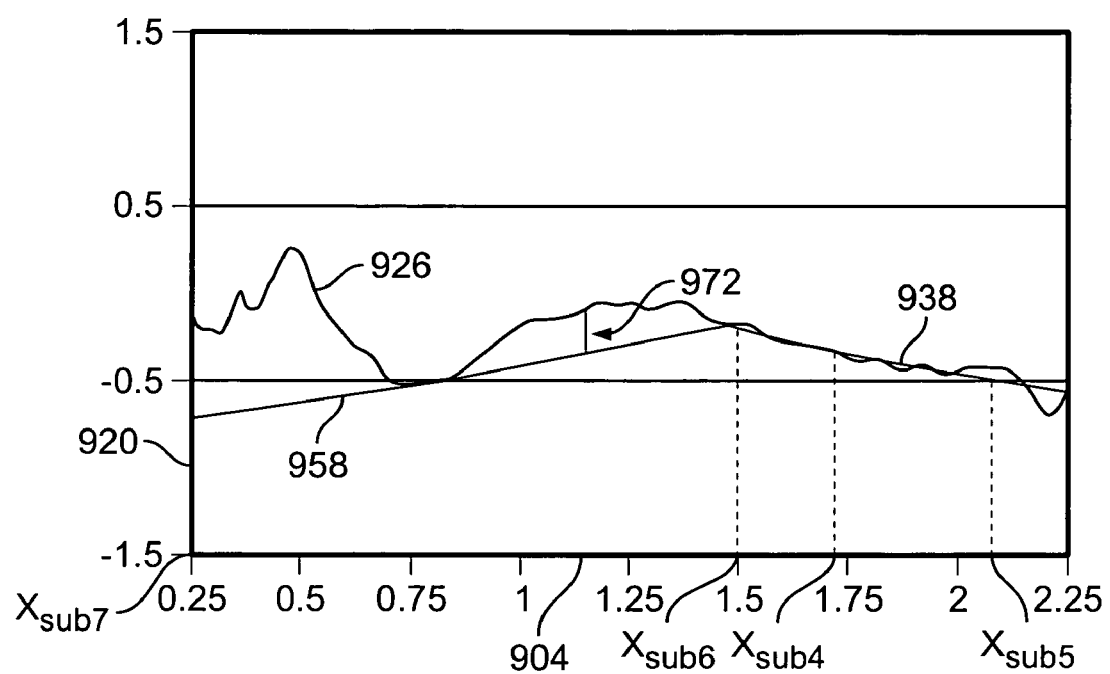

FIG. 15 shows a graph 926, which is a function $L_{sulphuric}(x)$ and an example of the function $L_{sub}(x)$. Processor 190 generates graph 926 as a logarithm, to the base e, of a ratio of a diffraction profile $D_{sulphuric}(x)$ of sulphuric acid and the diffraction profile $D_N(x)$ versus the momentum transfer x. Sulphuric acid ($H_2SO_4$) is an example of substance 82. Processor 190 plots $\log_e [D_{sulphuric}(x)/D_N(x)]$ on ordinate 920 and plots the momentum transfer x on abscissa 904.

Referring back to FIG. 7, processor 190 fits 930 a straight line $m_1 x+c_1$ to at least one value of $L_{sub}(x)$ within a range from and including $x_{sub4}$ to $x_{sub5}$ of the function $L_{sub}(x)$, where $m_1$ is a gradient of the straight line and $c_1$ is an intercept of the straight line with ordinate 920, $m_1$ may be a positive or a negative number, and $c_1$ may be a positive or negative number. An example of $x_{sub4}$ includes 1.5 $nm^{-1}$. Another example of $x_{sub4}$ includes 1.7 $nm^{-1}$. An example of $x_{sub5}$ includes 2.1 $nm^{-1}$. Another example of $x_{sub5}$ includes 2.3 $nm^{-1}$. As an example, processor 190 fits a straight line 936 (shown in FIG. 14) to all values of $L_{gas}(x)$ within a range from and including $x_{sub4}$ to $x_{sub5}$. As an example, processor 190 fits a straight line 938 (shown in FIG. 15) to all values of $L_{sulphuric}(x)$ within a range from and including $x_{sub4}$ to $x_{sub5}$. As still another example, processor 190 fits the straight line $m_1 x+c_1$ to all values of $L_{sub}(x)$ within a range from and including $x_{sub4}$ to $x_{sub5}$ by applying a linear regression fit to the values. As another example, processor 190 fits the straight line $m_1 x+c_1$ to all values of $L_{sub}(x)$ within a range from and including $x_{sub4}$ to $x_{sub5}$ by applying a weighted linear regression fit. In applying the weighted linear regression fit, processor 190 applies a higher weight to some of the values of $L_{sub}(x)$ within a range from and including $x_{sub4}$ to $x_{sub5}$ that are less noisy than to the remaining of the values that are more noisy. As yet another example, processor 190 divides all values of $L_{sub}(x)$ within a range from and including $x_{sub4}$ to $x_{sub5}$ into two windows. Processor 190 averages values of $L_{sub}(x)$ within each window and fits the straight line $m_1 x+c_1$ to the two average values. Each straight line 936 and 938 is an example of the straight line $m_1 x+c_1$.

Processor 190 may fit the straight line $m_1 x+c_1$ by applying a least squares fit approach. As another example, processor 190 determines the straight line $m_1 x+c_1$ that fits all values of $L_{sub}(x)$ between $x_{sub4}$ and $x_{sub5}$ by minimizing a sum of squares of perpendicular distances between the straight line and the values. As yet another example, processor 190 determines the straight line $m_1 x+c_1$ that fits all values of $L_{sub}(x)$ between $x_{sub4}$ and $x_{sub5}$ by minimizing a sum of squares of vertical distances between the straight line and the values. As yet another example, processor 190 fits the straight line $m_1 x+c_1$ to $L_{sub}(x)$ by determining that the straight line is connected to $L_{sub}(x)$ at $x_{sub4}$ and at $x_{sub5}$.

Processor 190 calculates 940 an effective atomic number $Z_{effsub}$ of substance 82 as a function of the gradient $m_1$ by applying $$m_1 = F(Z_{effsub}, Z_{effcalib}), \quad \text{Eq. (3)}$$

where $Z_{effcalib}$ is an effective atomic number of the calibration substance. Processor 190 determines the effective atomic number $Z_{effsub}$ of substance 82 by calculating 940 the effective atomic number $Z_{effsub}$ as a function of the gradient $m_1$ of the straight line $m_1 x+c_1$. The gradient $m_1$ of straight line $m_1 x+c_1$ is fitted, within a range of momentum transfer values, to the logarithmic profile ratio $L_{sub}(x)$ which is a function of the diffraction profiles $D_{sub}(x)$ and $D_{calib}(x)$ according to equation (2). The diffraction profile $D_{sub}(x)$ is a function of the momentum transfer x, which is generated from correction output signals 280, 282, 284, 286, 288, 290, 292, 294, 580, 582, 584, 586, 588, 590, 592, and 594 and the correction output signals are generated based on electrical output signals 196, 198, 200, 202, 204, 206, 208, 210, 212, 496, 498, 500, 502, 504, 506, 508, 510, and 512. Accordingly, the effective atomic number $Z_{effsub}$ is determined based on the electrical output signals 196, 198, 200, 202, 204, 206, 208, 210, 212, 496, 498, 500, 502, 504, 506, 508, 510, and 512.

The effective atomic number $Z_{effsub}$ is a function of the gradient $m_1$ of the straight line $m_1 x+c_1$, which is fitted to the logarithmic profile ratio $L_{sub}(x)$. The logarithmic profile ratio $L_{sub}(x)$ is a function of the diffraction profiles $D_{sub}(x)$ and $D_{calib}(x)$ according to equation (2). Accordingly, the effective atomic number is a function of the diffraction profiles $D_{sub}(x)$ and $D_{calib}(x)$.

Processor 190 receives the $Z_{effcalib}$ from a user via input device 192 and stores the $Z_{effcalib}$ in memory device 195. An example of $Z_{effcalib}$ is an atomic number of nitrogen. Another example of $Z_{effcalib}$ is an effective atomic number of the white scatterer.

Processor 190 determines the function F from substances with known effective atomic numbers. For example, a substance with known effective atomic number $Z_{known1}$ is scanned by using system 10 in the same manner as that of substance 82 to generate a plurality of electrical signals, which are received from scatter detectors 16 and 18. The substance with effective atomic number $Z_{known1}$ is a known substance. An example of the effective atomic number $Z_{known1}$ includes an atomic number of six for carbon. Another example of the effective atomic number $Z_{known1}$ includes an atomic number of eight for oxygen.

Processor 190 of system 100 receives a plurality of signals from scatter detectors 16 and 18 and executes 903 (shown in FIG. 6) on the known substance instead of substance 82 to generate a diffraction profile $D_{known1}(x)$ of the known substance. Processor 190 further calculates a ratio $D_{known1}(x)/D_{calib}(x)$ instead of calculating 914 ratio $D_{sub}(x)/D_{calib}(x)$, computes a $\log_e(D_{known1}(x)/D_{calib}(x))$ instead of computing 916 $\log_e(D_{sub}(x)/D_{calib}(x))$, and fits a straight line to at least one value of the ratio $\log_e(D_{known1}(x)/D_{calib}(x))$ between $x_{sub4}$ and $x_{sub5}$ instead of fitting 930, determines a gradient $m_{known1}$ of the straight line, and determines that the gradient $m_{known1}$ is a function $F_{known1}$, such as a best fit function, of the two effective atomic numbers $Z_{known1}$ and $Z_{effcalib}$. The function $F_{known1}$ corresponds to the effective atomic number $Z_{known1}$.

Processor 190 also determines a plurality of additional functions $F_{known2}, F_{known3}, F_{known4}, \ldots, F_{knownN}$ of N known substances with corresponding effective atomic numbers $Z_{known2}, Z_{known3}, \ldots, Z_{knownN}$ in the same manner as that of determining $Z_{known1}$ and creates a list of the functions $F_{known1}, F_{known2}, F_{known3}, F_{known4}, \ldots, F_{knownN}$ versus known effective atomic numbers $Z_{known1}, Z_{known2}, \ldots, Z_{knownN}$. Processor 190 determines the function F as a relationship, such as linear or polynomial, between the functions $F_{known1}, F_{known2}, F_{known3}, F_{known4}, \ldots, F_{knownN}$ and the known effective atomic numbers $Z_{known1}, Z_{known2}, \ldots, Z_{knownN}$.

Processor 190 determines an inverse function $F^{-1}$ and calculates 940 the effective atomic number $Z_{effsub}$ as a function of $m_1$ and $Z_{effcalib}$. For example, processor 190 calculates the effective atomic number $Z_{effsub}$ as $F^{-1}(m_1) + Z_{effcal}$, where $F^{-1}$ is the inverse of the function F. Processor 190 extrapolates 942 the straight line $m_1x + c_1$ from $X_{sub4}$ to a momentum transfer value $x_{sub6}$ shown in FIGS. 14 and 15. For example, processor 190 extrapolates straight line 938 (shown in FIG. 15) from $x_{sub4}$ to $x_{sub6}$ As another example, processor 190 extrapolates straight line 936 (shown in FIG. 14) from $x_{sub4}$ to $x_{sub6}$. An example of $x_{sub6}$ includes 1.5 nm$^{-1}$. Another example of $x_{sub6}$ includes 1.3 nm$^{-1}$. Another example of $x_{sub6}$ includes 2 nm$^{-1}$. Yet another example of $x_{sub6}$ includes $x_{sub4}$ in which case processor 190 does not need to extrapolate the straight line $m_1x + c_1$ from $x_{sub4}$ to $x_{sub6}$.

Processor 190 calculates 950 a negative of the gradient $m_1$ and generates 952 a straight line $m_2x + c_2$, where $m_2$ is a gradient of the straight line and $c_2$ is an intercept of the straight line with ordinate 920. As an example, $m_2 = -m_1$. As another example, $m_2 = -1.1 m_1$. An example of the straight line $m_2x + c_2$ is shown as a straight line 956 in FIG. 14. Another example of the straight line $m_2x + c_2$ is shown as a straight line 958 in FIG. 15.

Processor 190 extrapolates 962 the straight line $m_2x + c_2$ from $x_{sub6}$ to a momentum transfer value $x_{sub7}$ shown in FIGS. 14 and 15. An example of $x_{sub7}$ is 0 nm$^{-1}$. Another example of $x_{sub7}$ is 0.25 nm$^{-1}$. Processor determines 966 a difference between the function $L_{sub}(x)$ and a set of the straight lines $m_1x + c_1$ and $m_2x + c_2$. For example, processor 190 determines a vertical difference between the function $L_{sub}(x)$ between $x_{sub5}$ and $x_{sub6}$ and the straight line $m_1x + c_1$ between $x_{sub5}$ and $x_{sub6}$. In this example, processor 190 also determines a vertical difference between the function $L_{sub}(x)$ between $x_{sub6}$ and $x_{sub7}$ and the straight line $m_2x + c_2$ between $x_{sub6}$ and $x_{sub7}$. An example of a vertical difference between a value of $L_{sub}(x)$ and straight line 936 is a distance 970 shown in FIG. 14. Another example of a vertical difference between a value of $L_{sub}(x)$ and straight line 958 is a distance 972 shown in FIG. 15.

Processor 190 calculates 976 a relative molecular interference function $s_{relative}(x)$ as an antilog, which is an exponent of the difference between the function $L_{sub}(x)$ and the set of straight lines $m_1x + c_1$ and $m_2x + c_2$. The logarithmic profile ratio $L_{sub}(x)$ is a function of the diffraction profiles $D_{sub}(x)$ and $D_{calib}(x)$ according to equation (2). Moreover, the straight line $m_1x + c_1$ that is fitted to the logarithmic profile ratio $L_{sub}(x)$ is a function of the logarithmic profile ratio $L_{sub}(x)$. Furthermore, the straight line $m_2x + c_2$ determined based on the straight line $m_1x + c_1$ is also a function of the logarithmic profile ratio $L_{sub}(x)$. Accordingly, the relative molecular interference function $s_{relative}(x)$ is a function of the diffraction profiles $D_{sub}(x)$ and $D_{calib}(x)$. The relative molecular interference function is a ratio of a molecular interference $s_{sub}(x)$ of substance 82 to a molecular interference function $s_{calib}(x)$ of the calibration substance.

Processor 190 computes 978 the molecular interference function $s_{sub}(x)$ from the relative molecular interference function $s_{relative}(x)$ by multiplying the relative molecular interference function $s_{relative}(x)$ with the molecular interference function $s_{calib}(x)$. Processor 190 receives the molecular interference function $s_{calib}(x)$ from the user via input device 192 and stores the molecular interference function in memory device 195.

Figure 10:
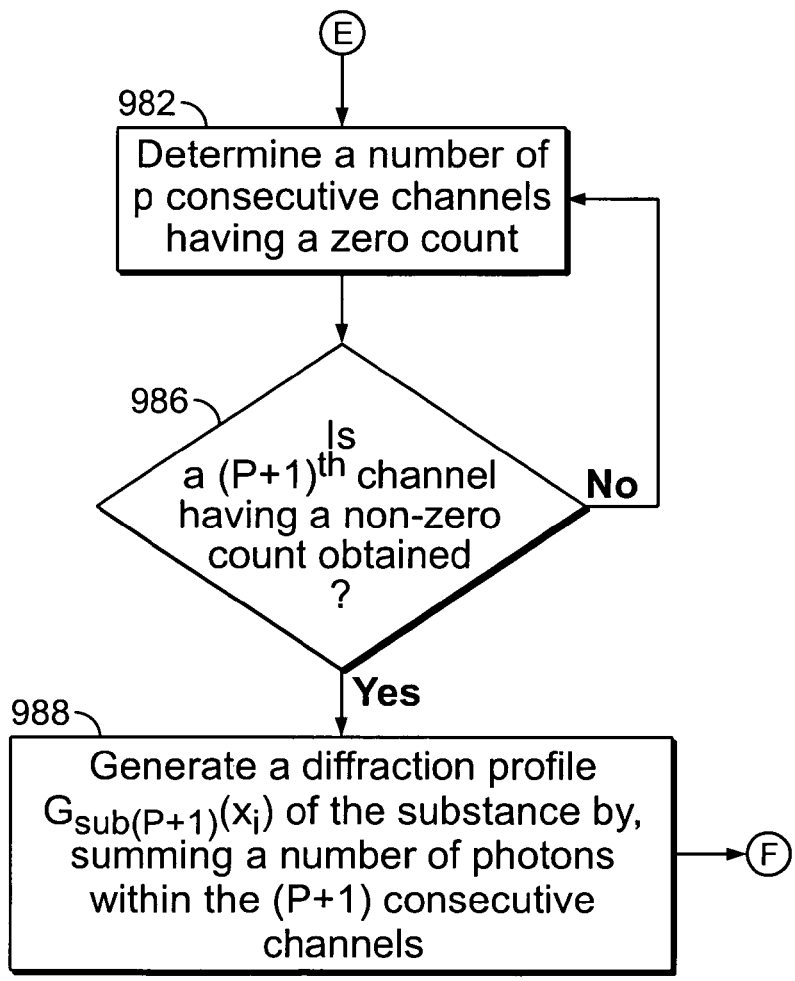
Figure 11:
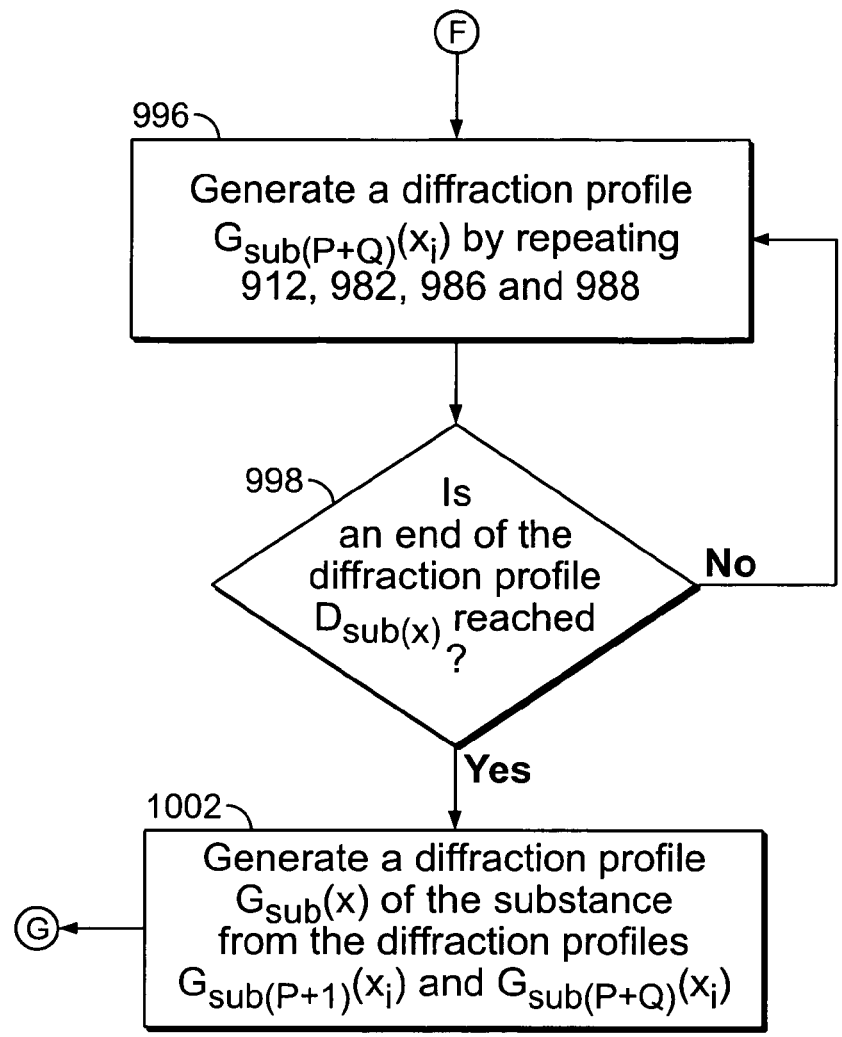
Figure 12:
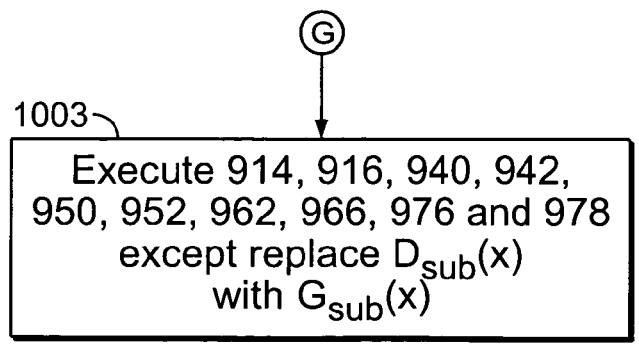

Referring to FIGS. 7 and 10, upon determining 912 (FIG. 7) that at least one channel of the diffraction profile $D_{sub}(x)$ has a zero count of photons, processor 190 determines 982 a number P of consecutive channels of the diffraction profile $D_{sub}(x)$, where each P channel has a zero count of photons. The consecutive channels have consecutive momentum transfer values. For example, one of the consecutive channels has a plurality of momentum transfer values ranging from 1.25 nm$^{-1}$ to 1.5 nm$^{-1}$ and another one of the consecutive channels has a plurality of momentum transfer values ranging from 1.5 nm$^{-1}$ to 1.6 nm$^{-1}$. As another example, one of the consecutive channels has a momentum transfer values of 1.2 nm$^{-1}$ and another one of the consecutive channels has a momentum transfer value of 1.3 nm$^{-1}$.

Processor 190 determines 982 the number of consecutive channels until processor 190 determines 986 that a $(P+1)^{th}$ channel of the diffraction profile $D_{sub}(x)$ having a non-zero count of photons is obtained. An example of the $(P+1)^{th}$ channel having a non-zero count of photons is a channel having a plurality of momentum transfer values ranging from the momentum transfer value $x_{sub4}$ to the momentum transfer value $x_{sub5}$. Another example of the $(P+1)^{th}$ channel having a non-zero photon count is a channel having the momentum transfer value $x_{sub4}$. The $(P+1)^{th}$ channel is consecutive to the $P^{th}$ channel. For example, if the $P^{th}$ channel has a plurality of momentum transfer values ranging from 1.5 nm$^{-1}$ to 1.4 nm$^{-1}$, the $(P+1)^{th}$ channel has a plurality of momentum transfer values ranging from 1.4 nm$^{-1}$ to 1.3 nm$^{-1}$. As another example, if the $P^{th}$ channel has a momentum transfer value of 1.4 nm$^{-1}$, the $(P+1)^{th}$ channel has a momentum transfer value of 1.3 nm$^{-1}$. Upon determining 986 that the $(P+1)^{th}$ channel of the diffraction profile $D_{sub}(x)$ having a non-zero count is obtained, processor 190 sums a number of photons within the P+1 channels of the diffraction profile $D_{sub}(x)$ by applying $$G_{sub(P+1)}(x_i) = \sum_{i=1}^{P+1} D_{sub}(x_i) \qquad \text{Eq. (4)}$$

where $G_{sub(P+1)}(x_i)$ is a diffraction profile of substance 82 for momentum transfer values between $x_1$ and $x_{P+1}$. Processor generates 988 the diffraction profile $G_{sub(P+1)}(x_i)$. An example of $x_i$, where i=1, is $x_{submax}$. Another example of $x_i$, where i=1, is $x_{sub0}$.

Processor 190 repeats techniques 912, 982, 986, and 988 to generate 996 a diffraction profile:

$$G_{sub(P+Q)}(x_i) = \sum_{i=P+2}^{P+Q} D_{sub}(x_i), \quad \text{Eq. (5)}$$

for the remaining channels of the diffraction profile $D_{sub}(x)$ until processor 190 determines 998 that an end of the diffraction profile $D_{sub}(x)$ is reached. $G_{sub(P+Q)}(x_i)$ is a diffraction profile of substance 82 for momentum transfer values ranging from $x_{P+2}$ to $x_{P+Q}$. An end of the diffraction profile $D_{sub}(x)$ is reached when P+Q is equal to $x_{sub0}$, where processor 190 determines 912 to start with $x_{submax}$.

Processor 190 generates 1002 a diffraction profile $G_{sub}(x)$ of substance 82 as $G_{sub(P+1)}(x_1)$ for momentum transfer value $x_1$ to $x_{P+1}$ and as $G_{sub(P+Q)}(x_1)$ for momentum transfer values $x_{P+2}$ to $x_{P+Q}$. Processor 190 executes techniques 914, 916, 930, 940, 942, 950, 952, 962, 966, 976, and 978, at 1003, except replaces $D_{sub}(x)$ with $G_{sub}(x)$. For example, processor 190 calculates a ratio $G_{sub}(x)/G_{calib}(x)$ instead of calculating 914 the ratio $D_{sub}(x)/D_{calib}(x)$. As another example, processor 190 executes techniques 916, 930, 940, 942, 950, 952, 962, 966, 976, and 978 by using the ratio $G_{sub}(x)/G_{calib}(x)$ instead of the ratio $D_{sub}(x)/D_{calib}(x)$ to generate an effective atomic number and to generate a molecular interference function of substance 82. Processor 190 determines the diffraction profile $G_{calib}(x)$ in the same manner as that of determining the diffraction profile $G_{sub}(x)$ except that the calibration system is placed within system 10 instead of substance 82.

In an alternative embodiment, processor 190 determines 912 to start with a channel having the momentum transfer value $x_{sub0}$. In a further alternative embodiment, an end of the diffraction profile $D_{sub}(x)$ is reached when $x_{P+Q}$ is equal to $x_{submax}$, where processor 190 determines 912 to start with $x_{sub0}$.

Techniques illustrated in FIGS. 6-12, in some instances, may be performed sequentially, in parallel, or in an order other than that which is described. For example, the technique of 905 may be performed before performing the technique of 903. It should be appreciated that not all of the techniques described are required to be performed, that additional techniques may be added, and that some of the illustrated techniques may be substituted with other techniques. For example, the technique of 978 may not be performed.

A technical effect of the herein described system and methods for characterizing a substance includes using at least a plurality of values of the function $L_{sub}(x)$ in a range from and including the momentum transfer value $x_{sub5}$ to the momentum transfer value $x_{sub6}$ to determine the effective atomic number $Z_{effsub}$ of the substance. The plurality of values of the function $L_{sub}(x)$ helps average a plurality of oscillations in a molecular interference function determined by other techniques. The plurality of values of the function $L_{sub}(x)$ represents a greater number of photons than a number of photons represented by a plurality of values of the diffraction profile $D_{sub}(x)$ within the range from and including $x_{sub1}$ to $x_{sub3}$. The greater number of photons provides a better estimate of the effective atomic number $Z_{effsub}$ than that provided by using the value of the diffraction profile $D_{sub}(x)$ within the range from and including $x_{sub1}$ to $x_{sub3}$.

The greater number of photons reduces an amount of noise that adversely affects a calculation of an effective atomic number of substance 82. The greater number of photons facilitates reducing any increase in the noise due to variations in a spectrum of intensities of X-rays output by X-ray source 12, any non-uniformity in efficiency of detection of primary beams 83 and 84 and scattered rays 88, 89, 90, 91 by scatter detectors 16 and 18, and/or any variation in incident angles 96, 97, 98, and 105 (shown in FIG. 1). Moreover, the greater number of photons facilitates reducing false alarms in characterizing substance 82 and enhances a detection rate of characterizing substance 82. Moreover, the normalization of the diffraction profile $D_{sub}(x)$ with the diffraction profile $D_{calib}(x)$ or the normalization of the diffraction profile $G_{sub}(x)$ with the diffraction profile $G_{calib}(x)$ reduces the amount of noise.

Another technical effect includes using a plurality of values of the function $L_{sub}(x)$ between the momentum transfer values $x_{sub5}$ and $x_{sub7}$ to determine the molecular interference function $s_{sub}(x)$. The plurality of values of the function $L_{sub}(x)$ represents a number of photons greater than a number of photons represented by values of the diffraction profile $D_{sub}(x)$ between the ranges from and including $x_{sub1}$ to $x_{sub3}$ and facilitates generation of a better approximation of the molecular interference function $s_{sub}(x)$ and than that generated by using the values of the diffraction profile $D_{sub}(x)$. Substance 82 can be characterized more accurately based on the more accurate values of $Z_{effsub}$ and $s_{sub}(x)$. Yet another technical effect includes avoiding chances of calculating a logarithm of zero by determining whether at least one channel of the diffraction profile $D_{sub}(x)$ has a zero count of photons, as shown in FIG. 7. The function $L_{sub}(x)$ is not defined if $D_{sub}(x)$ is equal to zero.

Exemplary embodiments of a system and methods for characterizing a substance are described above in detail. The system and methods are not limited to the specific embodiments described herein. For example, the methods may be used in combination with other inspection/detection systems.

While various embodiments of the invention have been described, those skilled in the art will recognize that modifications of these various embodiments of the invention can be practiced within the spirit and scope of the claims.

What is claimed is:

1. A method for characterizing an unknown substance, said method comprising:
normalizing a diffraction profile of the unknown substance against a diffraction profile of a calibration substance to generate a normalized diffraction profile;
transforming the normalized diffraction profile into a logarithm;
fitting a first straight line to the logarithm;
determining a first gradient of the first straight line; and
characterizing the unknown substance based on the first gradient.

2. A method in accordance with claim 1, wherein normalizing a diffraction profile of the unknown substance comprises determining a ratio function of the diffraction profile of the unknown substance and the diffraction profile of the calibration substance.

3. A method in accordance with claim 2, wherein transforming the normalized diffraction profile comprises calculating a logarithm of the ratio function.

4. A method in accordance with claim 1, further comprising determining that the first gradient is a second function of a difference between an effective atomic number of the unknown substance and an effective atomic number of the calibration substance.

5. A method in accordance with claim 1, further comprising determining that the first gradient is a second function of an effective atomic number of the unknown substance and an effective atomic number of the calibration substance.

6. A method in accordance with claim 5, further comprising generating an inverse of the second function.

7. A method in accordance with claim 6, wherein said determining the effective atomic number of the unknown substance comprises calculating the effective atomic number from the inverse of the second function.

8. A method in accordance with claim 1, further comprising determining a relative molecular interference function of the unknown substance by extrapolating the first straight line to a momentum transfer value.

9. A method in accordance with claim 1, further comprising:
  determining whether at least one channel P of the diffraction profile of the unknown material has a zero count of photons; and
  when the at least one channel P has the zero count of photons, determining a channel P+1 that has a non-zero count of photons, wherein the channel P+1 is consecutive to the at least one channel P; and
  summing a number of photons in the channel P+1; and
  generating a second diffraction profile using the sum of the number of photons, wherein the second diffraction profile is included in a range of the diffraction profile of the unknown substance.

10. A method in accordance with claim 1, further comprising determining a difference between the logarithm and the first straight line.

11. A method in accordance with claim 10, further comprising calculating a relative molecular interference function of the unknown substance as a function of the difference.

12. A method in accordance with claim 1, further comprising fitting a second straight line to the logarithm, wherein the second straight line is different than the first straight line.

13. A method in accordance with claim 12, further comprising determining the second gradient of the second straight line as a second function of the first gradient, wherein the second gradient is other than the first gradient.

14. A method in accordance with claim 1, further comprising acquiring the diffraction profile of the calibration substance by irradiating a white scatter object.

15. A method for characterizing an unknown substance, said method comprising:
  acquiring a first diffraction profile of the unknown substance;
  acquiring a second diffraction profile of a calibration substance; and
  calculating an effective atomic number of the unknown substance using the first diffraction profile and the second diffraction profile, wherein said calculating comprises calculating the effective atomic number from a ratio function of the first diffraction profile and the second diffraction profile.

16. A method for characterizing an unknown substance, said method comprising:
  acquiring a first diffraction profile of the unknown substance;
  acquiring a second diffraction profile of a calibration substance; and
  calculating a relative molecular interference function of the unknown substance using the first diffraction profile and the second diffraction profile, wherein calculating the relative molecular interference function comprises calculating the relative molecular interference function from a ratio function of the first diffraction profile and the second diffraction profile.

17. A system for characterizing an unknown substance, said system comprising:
  an X-ray source configured to generate X-rays;
  a detector configured to output a plurality of electrical signals by detecting the X-rays; and
  a processor coupled to said X-ray source and said detector, said processor configured to:
    normalize a diffraction profile of the unknown substance against a diffraction profile of a calibration substance to generate a normalized diffraction profile;
    transform the normalized diffraction profile into a logarithm;
    fit a first straight line to the logarithm;
    determine a first gradient of the first straight line; and
    characterize the unknown substance based on the first gradient.

18. A system in accordance with claim 17, wherein said processor is further configured to determine a ratio function of the diffraction profile of the unknown substance and the diffraction profile of the calibration substance.

19. A system in accordance with claim 18, wherein said processor is further configured to determine at least one of an effective atomic number and a relative molecular interference function using the first gradient.

* * * * *